(12) United States Patent
Aslanian et al.

(10) Patent No.: US 6,518,287 B2
(45) Date of Patent: Feb. 11, 2003

(54) SUBSTITUTED IMIDAZOLES AS DUAL HISTAMINE $H_1$ AND $H_3$ AGONISTS OR ANTAGONISTS

(75) Inventors: Robert G. Aslanian, Rockaway, NJ (US); Stuart Rosenblum, West Orange, NJ (US); Mwangi Wa Mutahi, Edison, NJ (US); Neng-Yang Shih, North Caldwell, NJ (US); John J. Piwinski, Clinton Township, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/955,380

(22) Filed: Sep. 18, 2001

(65) Prior Publication Data

US 2002/0103235 A1 Aug. 1, 2002

Related U.S. Application Data

(60) Provisional application No. 60/234,040, filed on Sep. 20, 2000.

(51) Int. Cl.$^7$ .................. A61K 31/4439; A61K 31/444; C07D 401/12; C07D 401/14; A61P 11/06; A61P 25/00

(52) U.S. Cl. ...................... 514/341; 514/333; 514/396; 514/399; 514/400; 546/256; 546/272.7; 546/275.1; 548/338.1; 548/300.1

(58) Field of Search ........................... 546/275.1, 272.7, 546/256; 514/341, 333, 396, 399; 548/338.1

(56) References Cited

U.S. PATENT DOCUMENTS

| | | | |
|---|---|---|---|
| 4,767,778 A | 8/1988 | Arrang et al. | |
| 5,352,707 A | 10/1994 | Pompni et al. | |
| 5,869,479 A | 2/1999 | Kreutner et al. | |
| 6,211,182 B1 * | 4/2001 | Vaccaro | 514/253.09 |

FOREIGN PATENT DOCUMENTS

| | | |
|---|---|---|
| EP | 0448 765 B1 | 3/1990 |
| EP | 0 420 396 B1 | 7/1990 |
| WO | WO 93/01812 | 2/1993 |
| WO | WO 93/12093 | 6/1993 |
| WO | WO 93/14070 | 7/1993 |
| WO | WO 95/14007 | 5/1995 |
| WO | WO 96/29315 | 9/1996 |
| WO | WO 98/58646 | 12/1998 |

OTHER PUBLICATIONS

Howson, Bioorganic & Medicinal Chemistry Letters, Two Novel, Potent and Selective Histamine H3 Receptor Agonists, vol. 2, pp. 77–78, 1992.

Stark, J. Med. Chem. , Novel Carbamates as Potent Histamine H3 Receptor Antagonists with High in Vitro and Oral In Vivo Activity, 39, pp. 1157–1163.

Sasse, Bioorganic & Medicinal Chemistry , (Partial) Agonist/Antagonist Properties of Novel Diarylalkyl, vol. 8 (2000) pp. 1139–1149.

Bagley, J. Med. Chem. 1991, New 1–(Heterocyclylalkyl)–4–(Propionanilido)–4–Piperidinyl, 34, pp 827–941.

Huls, Bioorganic & Medicinal Chemistry Letters, Diphenylmethyl Ethers: Synthesis and Histamine, vol. 6, No. 16, pp. 2013–2018, 1996.

Buschauer, J. Med. Chem. 1989, Synthesis and in Vitro Pharmacology of Arpromidine, 32, pp 1963–1970, 1989.

Schulze, Arch. Pharm. (Weinheim), Synthese und kombinierte H1/H2–antagonistische, vol. 327, pp. 455–462, 1994.

Schulze, European Journal of Pharmaceutical Sciences, Combined histamine H1/H2 receptor antagonists, vol. 6, pp. 177–186, 1998.

van der Goot, Eur J. Med. Chem. , Isothiourea analogues of histamine as potent agonists, vol. 27, pp. 511–517, 1992.

Walczynski, Il Farmco, Non–imidazole histamine H3 ligands, Vo. 54, pp. 684–694, 1999.

Brown, Br. J. Pharmac. , Pharmacological studies with SK & F 93944, vol. 87, pp. 569–578, 1986.

West, Molecular Pharmacology, Identificatin of Two H3–Histamine Receptor Subtypes, vol. 38, pp. 610–613, 1990.

Clapham, Brit. J. Pharm. Suppl. , Ability of the Selective Histamine H3 Receptor Antagonist, vol. 110, pp. Abs. 65P, 00/00, 1993.

Yokoyama, European Journal of Pharmacology, Effect of Thioperamide, vol. 234, pp 129–133, 1993.

Schlicker, Br. J. Pharmacol., Novel Histamine H3 Receptor Antagonists, vol. 112, pp. 1043–1048, 1994.

Leurs, Progre. Drug. Res. , The Histamine H3 Receptor, vol. 39, pp. 127–165, 00/00, 1992.

Lipp, Histamine Receptor, Pharmacochemistry of H3–Receptors, pp. 57–72, 00/00, 1992.

Stark, European Journal of Pharmaceutical Sciences, New potent Histamine H3–Receptor vol. 3, pp. 95–104, 1995.

Huls, A., Bio. & Med. Chem. Ltrs., vol. 6, No. 16, Diphenylmethyl Ethers, pp. 2013–2018, 1996.

Muller, M., Arch. Pharm. Pharm. Med. Chem, vol. 330, Synthesis and Neuropeptide Y Y1 receptor Antagonistic Activity, pp 333–342 (1997).

(List continued on next page.)

*Primary Examiner*—Evelyn Mei Huang
(74) *Attorney, Agent, or Firm*—Palaiyur S. Kalyanaraman

(57) ABSTRACT

The present invention discloses novel substituted imidazole compounds which have either or dual histamine-$H_1$ and $H_3$ receptor antagonist activity as well as methods for preparing such compounds. In another embodiment, the invention discloses pharmaceutical compositions comprising such imidazoles as well as methods of using them to treat allergy, inflammatory and CNS-related diseases and others.

15 Claims, No Drawings

OTHER PUBLICATIONS

Sasse, A., Bioorganic & Medicinal Chemistry, vol. 8, (Partial) Agonist/Antagonist Properties, pp. 1139–1149 (2000).

Schuhack, A., Biomedical & Health Research Programme of European Union, Benzhydryl Ethers Possessing Combined Histamine H3–H1 Receptor Antagonist Activity, p. 5117 (1996).

Stark, H., Eur. J. Med. Chem, vol. 29, Acylated and alkylated histamine derivatives as new histamine H3–receptor antagonists, pp. 695–700 (1994).

Stark, H., Eur. J. of Pharm. Sci, vol. 3, New Potent Histamine H3–receptor antagonists of the amide type, pp. 95–104 (1995).

Stark, H., Arch. Pharm. Med. Chem., vol. 331, Development of FUB 181, a Selective Histamine H3–Receptor Antagonist, pp. 211–218 (1998).

Stark, H., Drugs of the Future, vol. 21(5), Developments of Histamine H3–receptor antagonists, pp. 507–520 (1996).

* cited by examiner

SUBSTITUTED IMIDAZOLES AS DUAL HISTAMINE $H_1$ AND $H_3$ AGONISTS OR ANTAGONISTS

The invention disclosed in this application claims priority from provisional application, Ser. No. 60/234,040 filed Sep. 20, 2000, and is related to that in pending provisional applications, Ser. No. 60/234,039, Ser. No. 60/234,038, and Ser. No. 60/234,053, all filed on Sep. 20, 2000.

FIELD OF THE INVENTION

The present invention relates to novel substituted imidazole compounds having valuable pharmacological properties, especially against inflammatory diseases and allergic conditions. Compounds of this invention are antagonists of the histamine receptors. Some are antagonists of the histamine-$H_1$ receptors. Some are antagonists of the histamine-$H_3$ receptors. Some are antagonists of both the $H_1$ and $H_3$ receptors, in other words dual $H_1$ and $H_3$ receptor antagonists.

BACKGROUND OF THE INVENTION

The histamine receptors, $H_1$, $H_2$ and $H_3$ are well-identified forms. The $H_1$ receptors are those that mediate the response antagonized by conventional antihistamines. $H_1$ receptors are present, for example, in the ileum, the skin, and the bronchial smooth muscle of humans and other mammals. A well known antagonist of $H_1$ receptors is loratadine, commercially available under the tradename CLARITIN® from Schering-Plough Corporation, Madison, N.J. Through $H_2$ receptor-mediated responses, histamine stimulates gastric acid secretion in mammals and the chronotropic effect in isolated mammalian atria.

$H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates nonepinephrine outflow to resistance and capacitance vessels, causing vasodilatation.

U.S. Pat. No. 4,767,778 (Arrang et al.) discloses certain imidazoles that behave as agonists of the $H_3$ receptors in rat brain. European Patent Application No. 0 420 396 A2 (Smith Kline & French Laboratories Limited) and Howson et al. (*Bioorg. & Med. Chem. Letters*, (1992), Vol. 2 No.1, pages 77–78) describe imidazole derivatives having an amidine group as $H_3$ agonists. Van der Groot et al. (*Eur. J. Med. Chem.* (1992) Vol. 27, pages 511–517) describe isothiourea analogs of histamine as potent agonists or antagonists of the histamine-$H_3$ receptor, and these isothiourea analogs of histamine overlap in part with those of the two references cited above. Clapham et al.. ["Ability of Histamine-$H_3$ Receptor Antagonists to Improve Cognition and to Increase Acetylcholine Release in vivo in the Rat", *British Assn. for Psychopharmacology*, Jul. 25–28 (1993), reported in *J. Psychopharmacol.* (Abstr. Book), A17] describe the ability of histamine-$H_3$ receptor antagonists to improve cognition and to increase release of acetylcholine in vivo in the rat. Clapham et al.. ["Ability of the selective Histamine-$H_3$ Receptor Antagonist Thioperamide to improve Short-term Memory and Reversal Learning in the Rat", *Brit. J. Pharm. Suppl.*, 1993, 110, Abstract 65P] present results showing that thioperamide can improve short-term memory and reversal learning in the rat and implicate the involvement of $H_3$ receptors in the modulation of cognitive function. Yokoyama et al.. ["Effect of Thioperamide, a Histamine-$H_3$ Receptor Antagonist, on Electrically Induced Convulsions in Mice", *Eur. J. Pharmacol.*, (1993), Vol. 234, pages 129–133] report how thioperamide decreased the duration of each phase of convulsion and raised the electroconvulsive threshold, and go on to suggest that these and other findings support the hypothesis that the central histaminergic system is involved in the inhibition of seizures. International Patent Publication No. WO 9301812-A1 (SmithKline Beecham PLC) describes the use of S-[3-(4(5)-imidazolyl)propyl] isothiourea as a histamine-$H_3$ antagonist, especially for treating cognitive disorders, e.g. Alzheimer's disease and age-related memory impairment. Schlicker et al. ["Novel Histamine-$H_3$ Receptor Antagonists: Affinities in an $H_3$ Receptor Binding Assay and Potencies in Two Functional $H_3$ Receptor Models", *British J. Pharmacol.*, (1994), Vol.112,1043–1048] describe a number of imidazolylalkyl compounds wherein the imidazolylalkyl group is bonded to a guanidine group, an ester group, an amide group, a thioamide group and a urea group, and compared these to thioperamide. Leurs et al. ["The Histamine-$H_3$-receptor: A Target for Developing New Drugs", *Progr. Drug Res.* (1992), Vol. 39, pages 127–165] and Lipp et al. ["Pharmacochemistry of $H_3$-receptors" in *The Histamine Receptor*, eds.: Schwartz and Haas, Wiley-Liss, New York (1992), pages 57–72] review a variety of synthetic $H_3$ receptor antagonists, and Lipp et al. (ibid. ) have proposed the necessary structural requirements for an $H_3$ receptor antagonist.

WO 95/14007 claims $H_3$ receptor antagonists of the formula

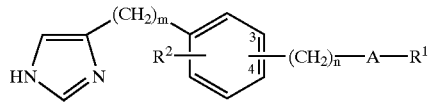

wherein A, m, n, $R^1$ and $R^2$ are defined therein. The compounds are disclosed as being useful for treating various disorders, in particular such caused by allergy-induced responses.

WO 93/12093 discloses imidazolylmethyl piperazines and diazepines as $H_3$ antagonists. U.S. patent application, Ser. No. 08/965,754, filed Nov. 7, 1997, discloses imidazolylalkyl substituted heterocyclic ring compounds as $H_3$ receptor antagonists. U.S. patent application, Ser. No. 08/966,344, filed Nov. 7, 1997, discloses phenylalkylimidazoles as $H_3$ receptor antagonists.

WO 96/29315 (PCT/FR96/00432) discloses certain N-imidazolylalkyl compounds containing phenyl moieties attached.

Also disclosing $H_3$ receptor antagonists are: H. Stark et al, *Eur. J. of Pharmaceutical Sciences* (1995) 3, 95–104; H. Stark et al, *J. Med. Chem.*, (1996) 39, 1157–1163; H. Stark et al, *Arch Pharm. Pharm. Med. Chem.*, (1998) 331, 211–218; and A. Sasse et al, *Bioorganic & Medicinal Chem.*, (2000) 8, 1139–1149.

Reference is also made to J. R. Bagley et al.. *Journal of Medicinal Chemistry*, (1991), Vol. 34, 827–841, which discloses, among others, N-(imidazolylalkyl) substituted cyclic amine compounds useful as analgesics such as the amine compound with the formula:

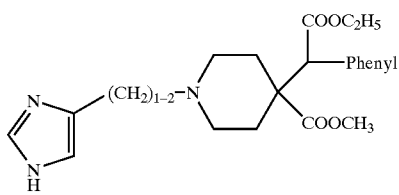

Pending U.S. patent application, Ser. No. 09/173,642, filed Oct. 16, 1998 (R. Wolin et al.), U.S. Pat. No. 6,133,291 discloses N-(imidazolylalkyl) substituted cyclic amine compounds having $H_3$ antagonist activity.

A. Huls et al., *Bioorg. & Med.Chem. Letters,* 6 (1996), 2013–2018 disclose imidazole compounds containing diphenyl ether moieties as $H_3$ receptor antagonists. The compounds are additionally disclosed to have $H_1$ receptor antagonist activity. An example compound from that publication is:

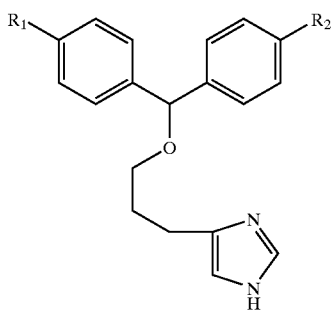

where $R_1$ and $R_2$ are defined therein.

A. Buschauer, *J. Med. Chem.,* 32 (1989), 1963–1970 disclose, among others, $H_2$ receptor antagonists of the type:

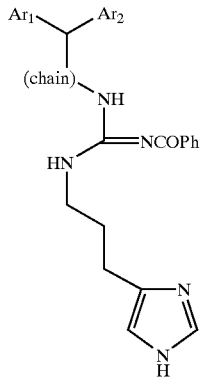

where $Ar_1$ and $Ar_2$ may be phenyl and/or pyridyl. EPO 448,765 A1 (published Mar. 30, 1990) discloses neuropeptide-Y antagonist imidazoles of the type:

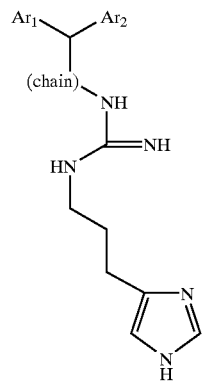

where $Ar_1$ and $Ar_2$ may be phenyl and/or pyridyl.
WO 98-58646 (assigned to Novo Nordisk A/S) discloses somatostatin SSTR4 receptor antagonist compounds of the type:

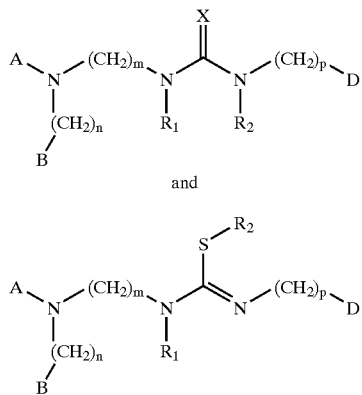

and wherein m is 2–6; n is 1–3; p is 1–6; $R_1$ and $R_2$ are independently H or C1–C6 alkyl optionally substituted with halogen, amino, hydroxy, alkoxy or aryl; X is S, O, NH, NCOPh or N(CN); A is aryl optionally substituted with halogen, amino, hydroxy, nitro, C1–6 alkyl, C1–6 alkoxy, or aryl; and B and D are independently aryl optionally substituted with halogen, amino, hydroxy, C1–6 alkyl, C1–6 alkoxy, or aryl.

Compounds have been reported in the literature as having activity against both $H_1$ and $H_2$ receptors, i.e. dual antagonists against $H_1$ and $H_2$ receptors. Thus, for example, F. Schulze et al., *European J. of Pharmaceutical Sciences,* 6 (1998), 177–186 report combined $H_1/H_2$ receptor antagonists. Other references in this category include F. Schulze et al., *Arch Pharm. (Weinheim),* 327 (1994), 455–462; C. Wolf et al., *Arch Pharm. Med. Chem.,* 329 (1996), 87–94; and C. Wolf et al., *European J. of Pharmaceutical Sciences,* 6 (1998), 177–186. Non-imidazole histamine $H_3$ ligands, particularly substituted benzothiazole derivatives as $H_3$ antagonists and $H_1$ blocking activities have been reported by K. Walczynski et al. *Il Farmaco,* 54 (1999), 684–694.

It would be useful to have compounds which are therapeutically effective as antagonists of both the $H_1$ and $H_3$ histamine receptors. The only such reported activity has been through a combination of two different chemical entities, one showing activity against $H_1$ receptors and the other showing activity against $H_3$ receptors. Thus, for example, U.S. Pat. No. 5,869,479 (issued Feb. 9, 1999 to Schering Corporation) discloses the combination of a histamine-$H_1$ receptor antagonist and a histamine-$H_3$ receptor antagonist for the treatment of allergy-induced airway responses.

Pending provisional patent application, Serial No.60/234,039, filed Sep. 20, 2000, discloses novel imidazole compounds having $H_3$ as well as dual $H_1$ and $H_3$ antagonist activity. The compounds disclosed therein have general formula in which an imidazole is linked to two cyclic moieties via intermediary moiety or moieties at least one of which intermediary moiety or moieties is a cyclic moiety.

Pending provisional patent application, Serial No. 60/234,038, filed Sep. 20, 2000, discloses novel imidazole compounds having $H_3$ as well as dual $H_1$ and $H_3$ antagonist activity. The compounds disclosed therein have general formula in which an imidazole is linked to a tricyclic moiety via intermediary moiety or moieties which intermediary moiety or moieties are all acyclic moieties.

Pending provisional patent application, Serial No. 60/234,053, filed Sep. 20, 2000, discloses novel imidazole compounds having $H_3$ as well as dual $H_1$ and $H_3$ antagonist activity. The compounds disclosed therein have general formula in which an imidazole is linked to a tricyclic moiety via intermediary moiety or moieties at least one of which intermediary moiety or moieties is a cyclic moiety.

It would be a welcome contribution to the art to have novel substituted imidazole compounds.

It would be useful to have the same chemical entity showing $H_3$ receptor activity as well as dual activity against both $H_1$ and $H_3$ receptors.

It would be useful to have novel substituted imidazoles showing $H_3$ receptor activity as well as dual activity against both $H_1$ and $H_3$ receptors.

This invention provides just such a contribution by providing novel substituted imidazole compounds having dual $H_1$ and $H_3$ antagonist activity.

SUMMARY OF THE INVENTION

In one embodiment, this invention provides novel substituted imidazole compounds having $H_3$ antagonist activity as well as dual $H_1$ and $H_3$ antagonist activity. The inventive compounds are substituted imidazoles wherein the imidazole is linked to two cyclic moieties via intermediary moiety or moieties which intermediary moiety or moieties are all acyclic. The compounds have the general structure shown in Formula I, including enantiomers, stereoisomers and tautomers thereof, as well as its pharmaceutically acceptable salts or solvates:

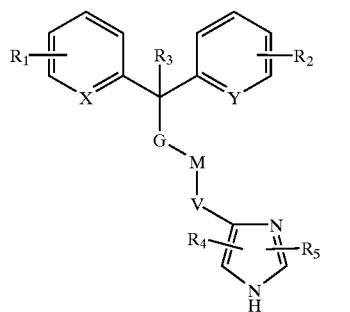

Formula I wherein
G is selected from the group consisting of $C_1$–$C_6$ alkyl or a bond;
M is a moiety selected from the group consisting of —C=C—, —C≡C—, —C(=NR$^7$)—NR$^6$—, —NR$^6$—C(=NR$^7$)—, —NR$^6$—C(O)—NR$^6$—, —NR$^6$—C(O)—O—, —O—C(O)—NR$^6$—, —NR$^6$—C(O)—, —C(O)—NR$^6$—, —O—, —NR$^6$—, —C(O)—, —N$^{30}$ R$^6$R$^8$—, and

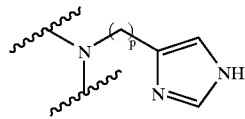

p is 1–6
V is $C_1$–$C_6$ alkyl;
X and Y may be the same or different and are independently selected from the group consisting of N, CH, or N-oxide, with the proviso that at least one of X and Y is N or N-oxide;
$R^1$ and $R^2$ may each number 1–4 and are independently selected from the group consisting of hydrogen, lower alkyl, lower alkoxy, halogen, polyhalolower alkyl, —OH, —N(R$^6$)$_2$, —NO$_2$, —CN, —COOR$^6$, —CONR$^6$R$^8$, and —NR$^6$—C(O)—R$^7$(wherein R$^7$ is not —OH or —CN);
$R^3$ is selected from hydrogen, lower alkyl, lower alkoxy, hydroxyl, polyhalolower alkyl, and a bond forming a double bond towards the moiety G when G is $C_1$–$C_6$ alkyl;
$R^4$ and $R^5$ are independently selected from the group consisting of hydrogen, lower alkyl, and polyhalolower alkyl;
$R^6$ and $R^5$ are independently selected from hydrogen, lower alkyl, aralkyl, alkylaryl, polyhalolower alkyl, substituted or unsubstituted phenyl; and substituted or unsubstituted benzyl; and
$R^7$ is selected from H, OH, alkoxy, cyano, phenyl, substituted phenyl, benzyl, and substituted benzyl;

with the proviso that when G is a bond and when M is either —O— or —O—C(O)—NR$^6$—, then one of X and Y is N; and with the further proviso that when $R^3$ is —OH or alkoxyl, and G is a bond, then M≠O or NR$^6$.

When used herein, the following terms have the given meanings:

lower alkyl (including the alkyl portions of lower alkoxy)—represents a straight or branched, saturated hydrocarbon chain having from 1 to 6 carbon atoms, preferably from 1 to 4. The term "alkyl" may also refer to moieties such as alkylenes and related moieties that are chemically suitable. Thus, for example, the definition of G and V may also include moieties such as ethylene, butylenes, —CH$_2$—CH(CH$_3$)—, —CH$_2$—C(=CH$_2$)— and the like;

aryl—represents a carbocyclic group having from 6 to 14 carbon atoms and having at least one benzenoid ring, with all available substitutable aromatic carbon atoms of the carbocyclic group being intended as possible points of attachment. Preferred aryl groups include 1-naphthyl, 2-naphthyl and indanyl, and especially phenyl and substituted phenyl;

aralkyl—represents a moiety containing an aryl group linked to the main group via an intermediary lower alkyl;

alkylaryl—represents a moiety containing a lower alkyl linked to the main group via an intermediary aryl group;

cycloalkyl—represents a saturated carbocyclic ring having from 3 to 8 carbon atoms, preferably 5 or 6, optionally substituted.

heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms, e.g., 2- or 3-piperidinyl, 2- or 3-piperazinyl, 2- or 3-morpholinyl, or 2- or 3-thiomorpholinyl;

halogen—represents fluorine, chlorine, bromine and iodine;

heteroaryl—represents a cyclic organic group having at least one O, S and/or N atom interrupting a carbocyclic ring structure and having a sufficient number of delocalized pi electrons to provide aromatic character, with the aromatic heterocyclic group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc. Preferred heteroaryl groups are 2-, 3- and 4-pyridyl; Such heteroaryl groups may also be optionally substituted.

The term "substituted", unless otherwise defined, refers to chemically suitable substitution with moieties such as, for example, alkyl, alkoxy, —$CF_3$, halogen or aryl.

Furthermore, the term "alkyl", when chemically suitable, also includes alkylene and related moieties. Thus, for example, the above-described definitions for G and V, could also include moieties such as, for example, ethylene, butylene, —$CH_2$—$CH(CH_3)$—, —$CH_2$—$C(=CH_2)$—, and the like.

Also included in the invention are tautomers, enantiomers and other optical isomers of compounds of Formula I, as well as pharmaceutically acceptable salts and solvates thereof.

A further feature of the invention is pharmaceutical compositions containing as active ingredient a compound of Formula I (or its salt, solvate or isomers) together with a pharmaceutically acceptable carrier or excipient.

The invention also provides methods for preparing compounds of Formula I, as well as methods for treating diseases such as, for example, inflammation, allergy, diseases of the GI-tract, cardiovascular disease, or disturbances of the central nervous system as well as allergy-induced airway (e.g., upper airway) responses, decongestion and obesity. The methods for treating comprise administering to a mammalian patient (including humans and animals) suffering from said disease or diseases a therapeutically effective amount of a compound of Formula I, or pharmaceutical compositions comprising a compound of Formula I.

DETAILED DESCRIPTION OF THE INVENTION

In one embodiment, the present invention provides novel imidazole compounds of Formula I:

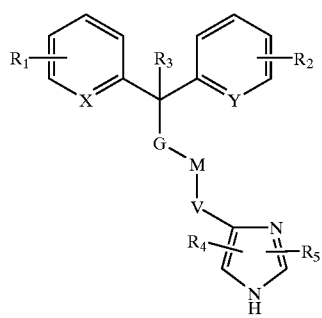

Formula I where the various symbols are as defined above. Representative compounds of the invention which exhibit excellent $H_3$ antagonist activity are listed below.

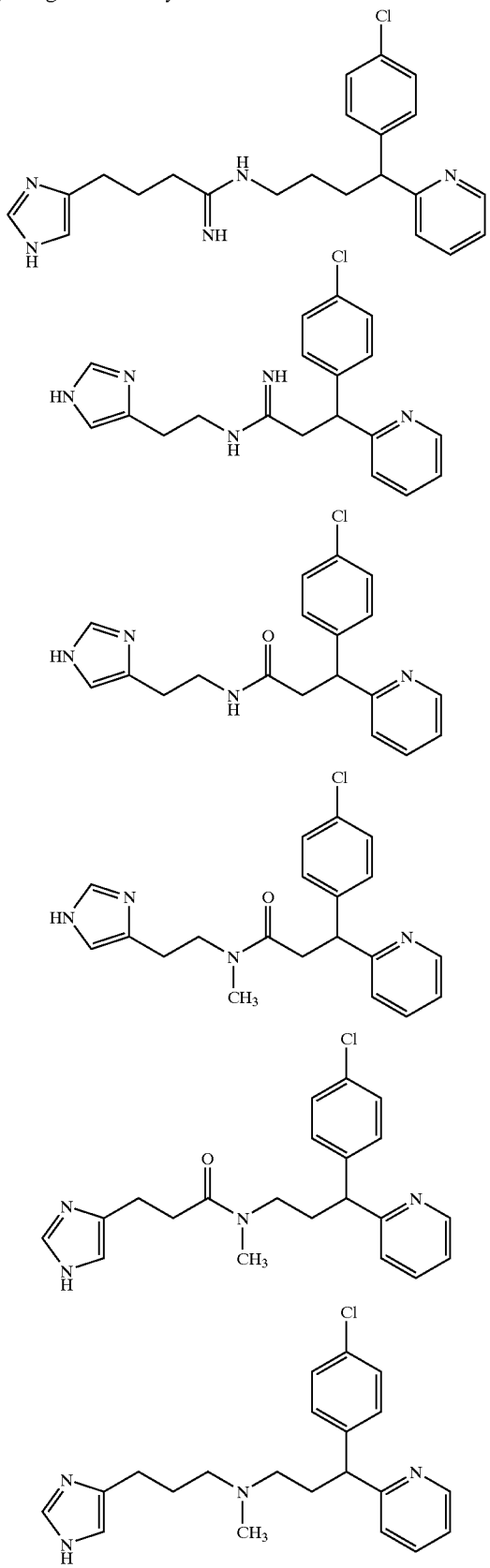

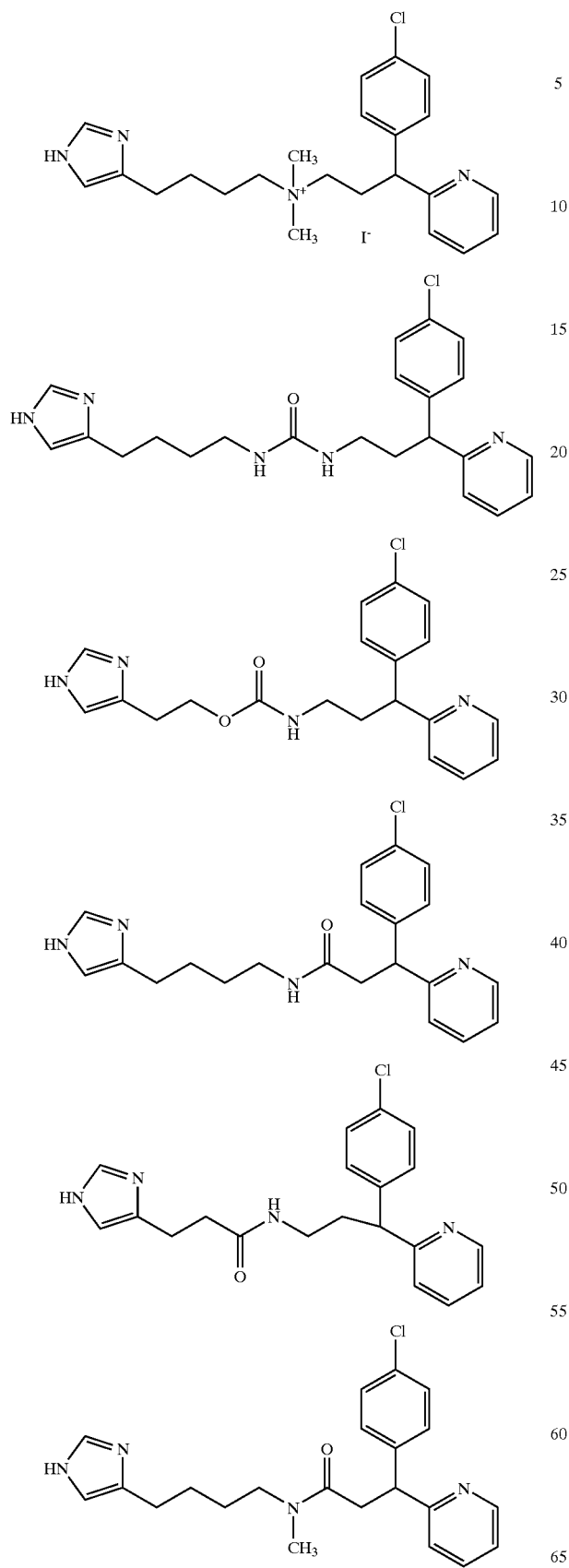
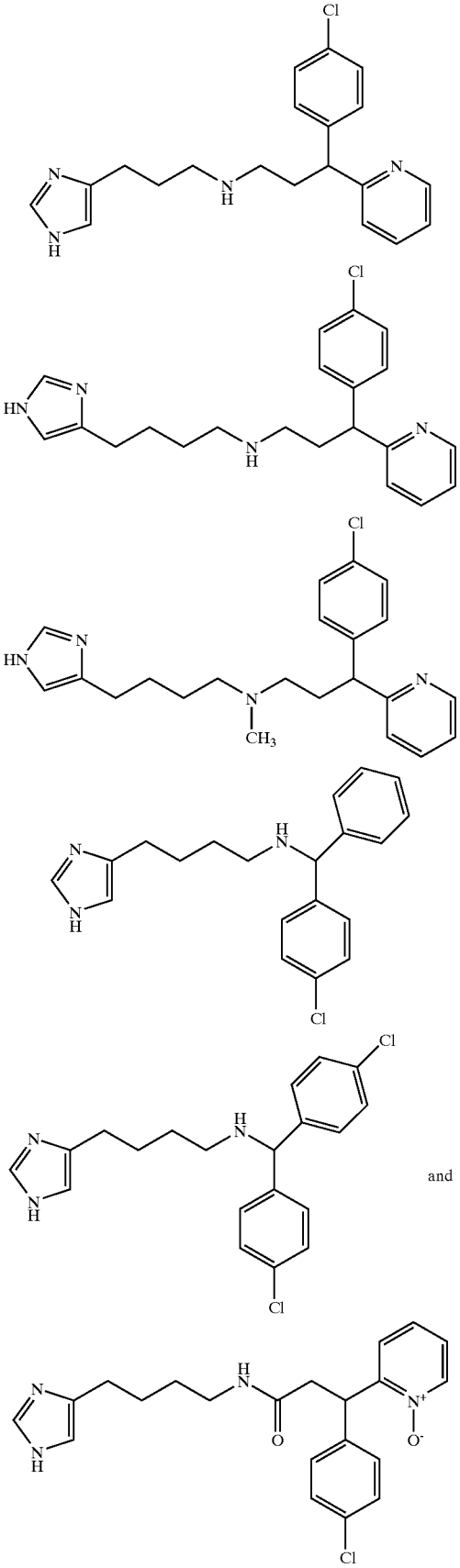

Some examples of compounds exhibiting both (or dual) $H_1$ and $H_3$ activity include:

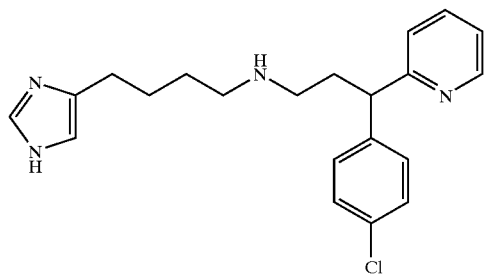

and

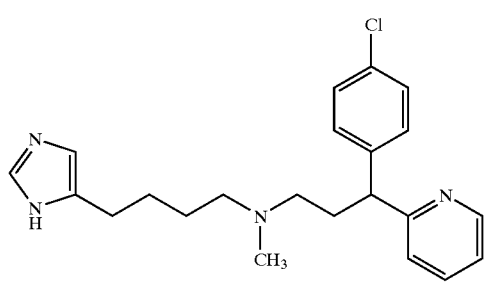

The compounds of the invention are basic and form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

Depending upon the substituents on the inventive compounds, one may be able to form salts with bases too. Thus, for example, if there are carboxylic acid substituents in the molecule, salts may be formed with inorganic as well as organic bases such as, for example, NaOH, KOH, $NH_4OH$, tetraalkylammonium hydroxide, and the like.

As stated earlier, the invention includes tautomers, enantiomers and other stereoisomers of the compounds also. Thus, as one skilled in the art knows, certain imidazole compounds may exist in tautomeric forms. Such variations are contemplated to be within the scope of the invention.

Another embodiment of the invention discloses a method of making the substituted imidazoles disclosed above. The compounds may be prepared by several processes well known in the art. In one method, the imidazole part (designated "the left side component" herein for simplicity purposes; see example below):

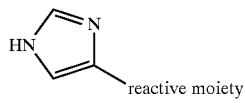

and the diaryl part (designated "the right side component" herein for simplicity purposes; see example below):

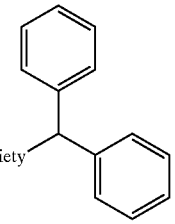

may be prepared separately. The left side component and the right side component may contain reactive moieties attached to them; these reactive moieties on the two components are suitable to be reacted with each other under appropriate reaction conditions. Thus, for example, the left side component may contain a carboxylic acid, and the right side component may have an amine end. Under appropriate reaction conditions, the two components may be reacted together whereby an imidazole containing a diaryl alkyl moiety linked through an extended amide chain is obtained. Other substituted imidazoles may similarly be prepared.

Isolation of the compound at various stages of the reaction may be achieved by standard techniques such as, for example, filtration, evaporation of solvent and the like. Purification of the product, intermediate and the like, may also be performed by standard techniques such as recrystallization, distillation, sublimation, chromatography, conversion to a suitable derivative which may be recrystallized and converted back to the starting compound, and the like. Such techniques are well known to those skilled in the art.

The thus prepared compounds may be analyzed for their composition and purity as well as characterized by standard analytical techniques such as, for example, elemental analysis, NMR, mass spectroscopy, and IR spectra.

The inventive compounds can readily be evaluated to determine activity at both $H_1$ and $H_3$ receptors by known methods, such as, for example, E. A. Brown et al, *British J. Pharm.*, (1986) Vol. 80, 569. $H_3$ activity may be determined by, for example, the guinea pig brain membrane assay and the guinea pig neuronal ileum contraction assay, both of which are described in U.S. Pat. No. 5,352,707. Another useful assay for $H_3$ activity utilizes rat brain membranes and is described by West et al., ("Identification of Two $H_3$-Histamine Receptor Subtypes", *Molecular Pharmacology*, (1990), Vol. 33, 610–613. Several of the present compounds were found to have high $H_1$ and $H_3$ antagonist activity which is discussed more in the EXAMPLES section below.

In another embodiment, this invention provides pharmaceutical compositions comprising the above-described inventive imidazoles as an active ingredient. The pharmaceutical compositions generally additionally comprise a pharmaceutically acceptable carrier diluent, excipient or carrier (collectively referred to herein as carrier materials). Because of their $H_1$ and $H_3$ antagonist activity, such pharmaceutical compositions possess utility in treating allergy, inflammation, nasal congestion, hypertension, glaucoma, sleeping disorders, states of hypermotility of the gastrointestinal tract, and hyperactivity of the central nervous system, Alzheimers, Schizophrenia, migraines, obesity and the like diseases.

In yet another embodiment, the present invention discloses methods for preparing pharmaceutical compositions comprising the inventive imidazole compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses use of the pharmaceutical compositions disclosed above for treatment of diseases such as, for example, allergy, inflammation, nasal congestion, hypertension, glaucoma, sleeping disorders, states of hypermotility of the gastrointestinal tract, hyperactivity of the central nervous system, Alzheimers, Schizophrenia, migraines, obesity and the like. The method comprises administering a therapeutically effective amount of the inventive pharmaceutical composition to a mammalian patient having such a disease or diseases and in need of such a treatment.

Those skilled in the art will realize that the term "upper airway" means the upper respiratory system—i.e., the nose, throat, and associated structures.

It will be apparent to those skilled in the art that many modifications, variations and alterations to the present disclosure, both to materials and methods, may be practiced. Such modifications, variations and alterations are intended to be within the spirit and scope of the present invention.

The following EXAMPLES are being provided to further illustrate the present invention. They are for illustrative purposes only; the scope of the invention is not to be considered limited in any way thereby.

EXAMPLES

Unless otherwise stated, the following abbreviations have the stated meanings in the Examples below:
DBU=1,8-diazabicyclo[5.4.0]undec-7-ene
DBN=1,5-diazabicyclo[4.3.0]non-5-ene
EDCI=1-(3-dimethylaminopropyl)-3-ethylcarbodiimide
HOBT=1-hydroxybenzotriazole
DCC=dicyclohexylcarbodiimide
Dibal-H=diisobutylaluminum hydride
LAH=lithium aluminum hydride
NaBH(OAc)$_3$=sodium triacetoxyborohydride
NaBH$_4$=sodium borohydride
NaBH$_3$CN=sodium cyanoborohydride
LDA=lithium diisopropylamide
p-TsOH=p-toluenesulfonic acid
m-CPBA=m-Chloroperbenzoic acid
TMAD=N,N,N',N'-tetramethylazodicarboxamide
CSA=camphorsulfonic acid
NaHMDS=sodium hexamethyl disilylazide
HRMS=High Resolution Mass Spectrometry
HPLC=High Performance Liquid Chromatography
LRMS=Low Resolution Mass Spectrometry
nM=nanomolar
K$_i$=Dissociation Constant for substrate/receptor complex
pA$_2$=−log EC$_{50}$, as defined by J. Hey, *Eur. J. Pharmacol.*, (1995), Vol. 294, 329–335.
Ci/mmol=Curie/mmol (a measure of specific activity)
Tr=Triphenylmethyl
Tris=Tris(hydroxymethyl)aminomethane Example 1

Preparation of Compound 2

(i) Preparation of Compound 1

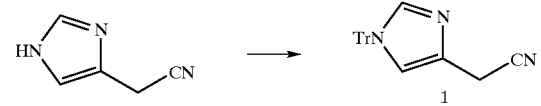

To a solution of commercially available 4-cyanomethylimidazole (Sigma Chemicals, St. Louis, Mo.)

(27 g) in DMF (450 mL), under argon and at room temperature, was added triphenylmethylchloride (73.9 g) and then triethylamine (52 mL). After stirring overnight, the reaction mixture was poured into ice/water (1.5 L). The thick white precipitate was collected by filtration, then dissolved in hot acetonitrile (500 mL) treated with activated carbon (DARCO), and filtered. The filtrate was cooled over ice water and the desired product (1) was obtained (64 g) as a white crystalline solid.

(ii) Preparation of Compound 2

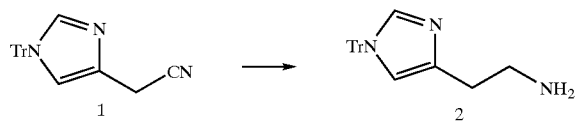

A solution of compound (1) (5 g) in $CH_3OH$ (200 mL) was treated with $CoCl_2.6H_2O$ (6.8 g), all at once, followed by portionwise addition of $NaBH_4$ (5.4 g) at room temperature. The resulting mixture was stirred for 1 h at room temperature. TLC (10% $NH_3$ sat $CH_3OH$ in $CH_2Cl_2$; product $R_f$=0.6) indicated completion of the reaction. The reaction mixture was concentrated under reduced pressure to remove $CH_3OH$ and extracted with $CH_2Cl_2$. The organic extracts were filtered through Celite and concentrated to afford a crude product. Purification on a silica gel flash column, eluting with 10% $NH_3$ saturated $CH_3OH$ in $CH_2Cl_2$, provided the title compound (2) (1.2 g) as a light-brown solid.

Example 2

Preparation of Compound 3

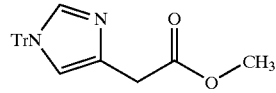

Commercially available 4-imidazoleacetic acid hydrochloride (Aldrich Chemicals, Milwaukee, Wis.) was esterified according to standard procedures, followed by tritylation in a manner similar to that described for the preparation of compound (1), to provide compound (3).

Example 3

Preparation of Compound 4

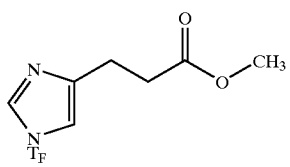

The literature compound, 3-(1(3)H-imidazol-4-yl) propionic acid methyl ester (Clitherow et al. *Bioorg. Med. Chem. Lett.* 8 (1996), 833–838) was tritylated as in Example 1(i) above to provide compound (4).

Example 4

Preparation of Compound 5

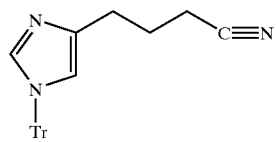

This was made according to the following literature reference: Stark, H.; Huels, A.; Ligneau, X.; Arrang, J.-M.; Schwartz, J.-C.; Schunack, W.; *Pharmazie*; EN; 52(7) (1997) 495–500.

Example 5

Preparation of Compound 6

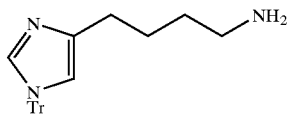

Compound 6 was prepared according to R. Wolin et al., *Bioorg. Med. Chem. Lett.* 8 (1998) 2157–2162.

Example 6

Preparation of Compound 7

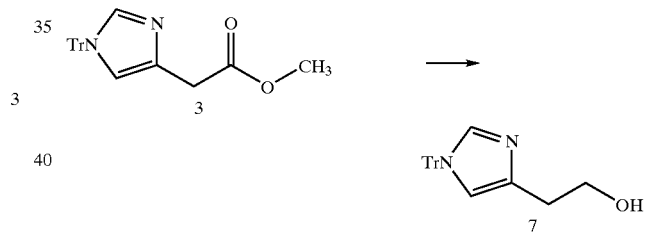

The product from Example 2 was reduced with LAH by standard procedures to provide the alcohol compound (7).

Example 7

Preparation of Compound 11

(i) Preparation of Compound 8

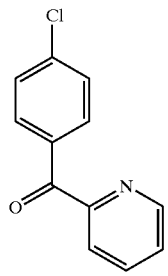

Commercially available 4-Bromochlorobenzene was treated with n-butyllithium to generate the lithium anion, followed by the addition of 2-cyanopyridine (from Aldrich Chemicals). Aqueous workup provided the desired diarylketone (8).

(ii) Preparation of Compound 9

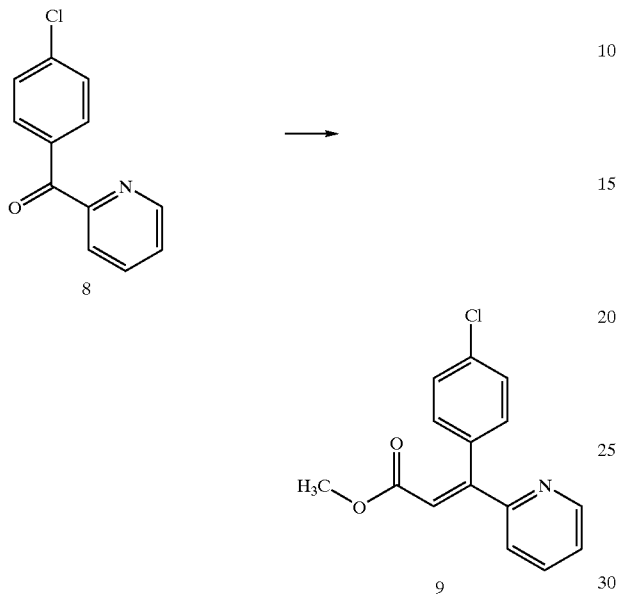

To a solution of NaHMDS (39.4 mL, 1 M in THF) at 0° C. was added dropwise over 10 min. neat trimethylphosphonoacetate (6.1 mL). The reaction was stirred for 20 min. at 0° C. and then left to warm up to room temperature. A solution of the ketone (8) (7.8 g) in THF (200 mL) was added to the reaction mixture and heated to 40° C. and stirred for 2 hr. TLC (30% ethyl acetate in hexane: product $R_f$=0.5 and 0.3) indicated completion of the reaction. The reaction was quenched with water (40 mL), concentrated and partitioned between water (200 mL) and ethyl acetate (200 mL). The organic layer was separated, washed with brine and dried over $Na_2SO_4$. The crude product was chromatographed on silica gel (30–50% ethyl acetate in hexane) to afford the desired product (9) as a light brown solid (9 g total yield: 4.5 g each for the E and Z isomers).

(iii) Preparation of Compound 10

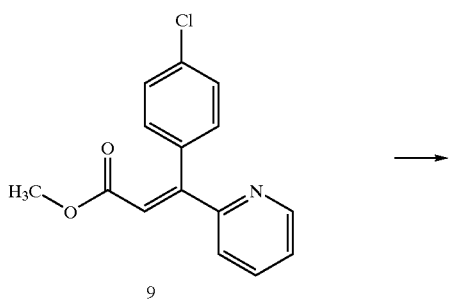

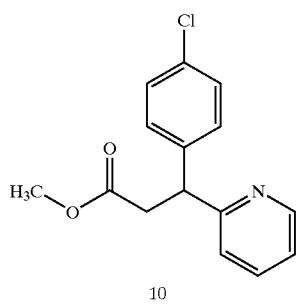

A solution of compound (9) (4.4 g) in MeOH (60 mL) was treated with acid activated magnesium (0.8 g) and stirred overnight at room temperature. The reaction mixture was then quenched with saturated aqueous $NH_4Cl$, partially concentrated, diluted with ethyl acetate, washed with brine, and dried over solid $Na_2SO_4$. Flash chromatography on silica gel provided the desired product (10) (2 g) as a white solid.

(iv) Preparation of Compound 11

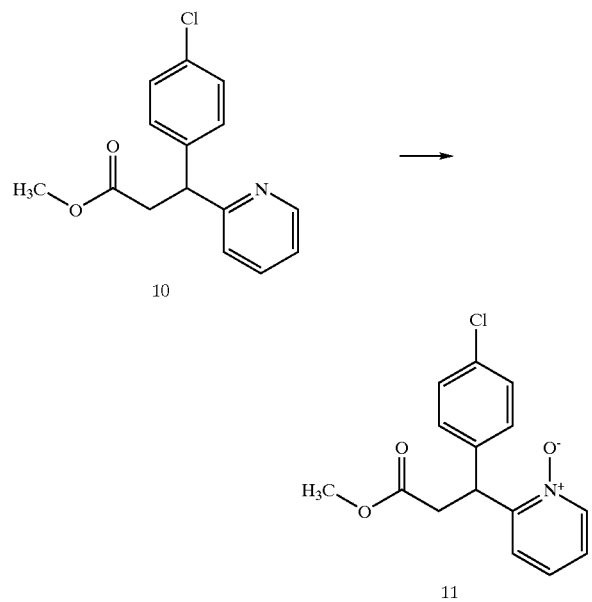

To a solution of m-chloroperbenzoic acid ("m-CPBA", 1.9 g) in $CH_2Cl_2$ (100 mL) was slowly added compound (10) (1 g). The reaction was stirred for 1 hr. at room temperature, then diluted with $CH_2Cl_2$ (100 mL) and washed sequentially with aqueous $NaHSO_3$ (5%), aqueous $NaHCO_3$, and water. It was dried over solid $MgSO_4$ and concentrated. The title compound was obtained quantitatively and was used without further purification. TLC (10% $CH_3OH$ in $CH_2Cl_2$); product $R_f$=0.7.

Example 8

Preparation of Compound 13

(i) Preparation of Compound 12

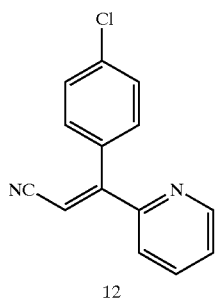

12

To a pentane-washed suspension of NaH (0.72 g, 60% suspension in mineral oil) in dry THF (30 mL) under argon and at 30° C. was added neat diethyl (cyanomethyl) phosphonate (from Aldrich Chemicals) (3.17 g) over 10 min. Hydrogen gas evolution was evident and after about 5 min., a clear solution resulted. After stirring for a total of 45 min. at room temperature, a solution of compound (8) (3 g) in dry THF (30 mL) was added. The reaction mixture turned deep-red and was stirred overnight at room temperature. TLC (20% isopropanol in hexane; product $R_f$=0.5) indicated completion of the reaction. The reaction mixture was concentrated and partitioned between water and $CH_2Cl_2$. The organic layer was separated and washed with 10% aq NaOH and dried over $MgSO_4$. Further purification by flash chromatography on silica gel (20% isopropanol in hexane) provided the desired product (12) (3 g, 90% yield) as a light-yellow powder.

(ii) Preparation of Compound 13

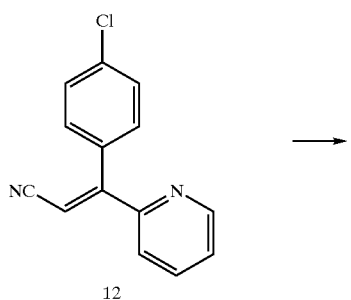

To a suspension of (12) (3 g) in dry isopropanol (90 mL) at room temperature was added solid $NaBH_4$ (4.72 g) and the reaction was refluxed for 2 days. The reaction changed color during this period from light-yellow to chocolate-red to pink. The reaction mixture was then concentrated and partitioned between water and $CH_2Cl_2$. The organic layer was isolated and dried with $MgSO_4$. Concentration and flash chromatography on silica gel (20% isopropanol in hexane) provided the title compound (13) (2.36 g, 78% yield) as a dark-red solid.

Example 9

Preparation of Compound 14

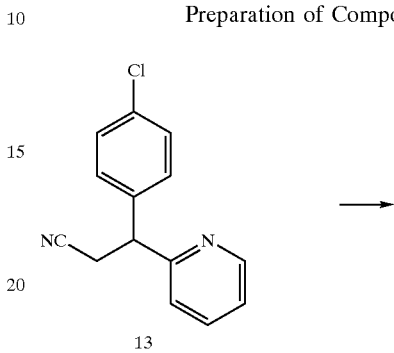

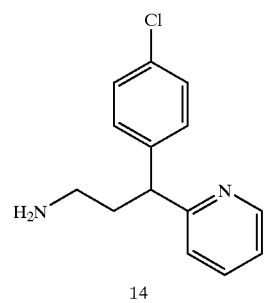

To LAH (21.4 mL, 1M suspension in ether) at 0° C. and under argon was added dropwise, over 5 min, a solution of (13) (2.36 g) in dry THF (100 mL). The resulting reaction mixture was refluxed overnight. The reaction was then cooled to room temperature and quenched successively with water (1 mL), aqueous 15% NaOH (1 mL), water (3 mL) and then filtered. The filtrate was dried with $MgSO_4$. Concentration and flash chromatography on silica gel (10% $NH_3$ saturated $CH_3OH$ in $CH_2Cl_2$; product $R_f$=0.4) provided the title compound (14) (0.87 g, 36% yield) as a reddish-brown thick oil.

Example 10

Preparation of Compound 15

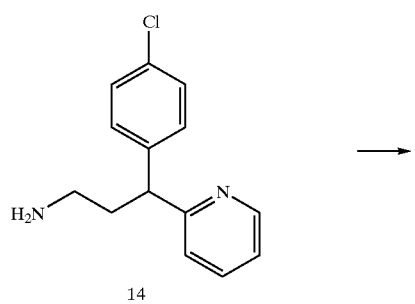

-continued

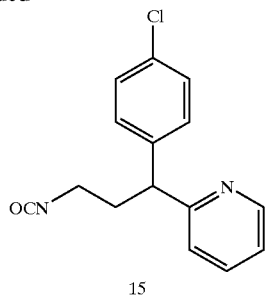

15

To a solution of triphosgene (3.96 g) in CH$_2$Cl$_2$ (30 mL) at 0° C. was added in one portion (14) (3 g) followed by dropwise addition of triethyl amine (5 mL) over 5 min. The resulting mixture stirred overnight at room temperature. This mixture was then filtered through a filter paper and concentrated. A deep blue solid of the crude isocyanate was obtained quantitatively and was used in the next reaction without further purification.

Example 11

Preparation of Compound 16

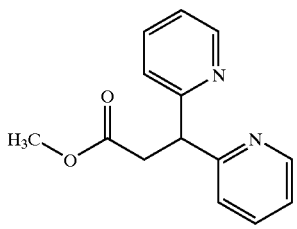

16

Compound (16) was made from the commercially available di-2-pyridyl ketone (from Aldrich Chemicals) following the procedure found in Example 7(iii).

Example 12

Preparation of Compound 17

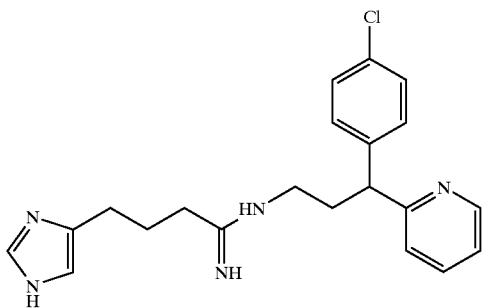

17

(i) To a solution of (CH$_3$)$_3$Al (2.06 mL, 2 M in hexane) was added (14) (0.51 g) in dry toluene (10 mL) dropwise over 5 min. After stirring the resulting mixture for about 45 min. at room temperature, nitrile (5) (0.78 g) in dry toluene (10 mL) was added dropwise over 5 min. The reaction was then heated to 100° C. and stirred overnight. After stirring overnight at 100° C., the reaction was cooled to room temperature and then a few drops of saturated aqueous Na$_2$SO$_4$ solution were added until gas bubbling had ceased whereupon solid Na$_2$SO$_4$ was added. The mixture was then filtered, concentrated and purified on a silica gel flash column, eluting with 1:2:7 diisopropylamine: NH$_3$ saturated CH$_3$OH:CH$_2$Cl$_2$. The crude product was dissolved in CH$_2$Cl$_2$ and filtered to remove any dissolved silica gel, reconcentrated and redissolved in toluene and then concentrated to remove any remaining diisopropyl amine.

(ii) All of the product from (i) above was dissolved in ethanol (40 mL), and treated with aqueous 1N HCl (32 mL) at 60° C. for 1 hr. The reaction mixture was then concentrated on the rotary evaporator to remove all the ethanol and diluted with water (20 mL). The precipitate was removed by filtration and the aqueous filtrate washed twice with ether (20 mL). The aqueous solution was then concentrated under reduced pressure to provide the title compound (17) (0.68 g, 68% yield from (i)) as a white crystalline solid; HRMS: M+1=382.1798, 382.1786.

Example 13

Preparation of Compound 18

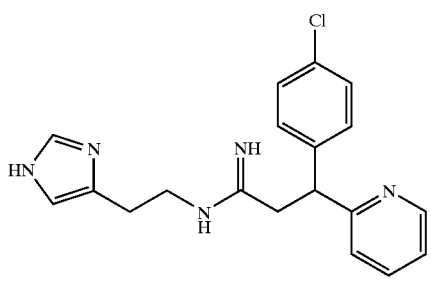

18

Compounds (2) and (13) were reacted following the same procedure as in Example 12, to afford the title Compound (18); HRMS: M+1=354.1485, 354.1490).

Example 14

Preparation of Compound 19

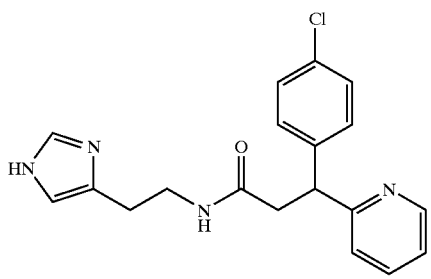

19

Compounds (2) and (10) were reacted following the same procedure as Example 12, to afford the title Compound (19); HRMS: M+1=355.1326, 355.1317.

Example 15

Preparation of Compound 20

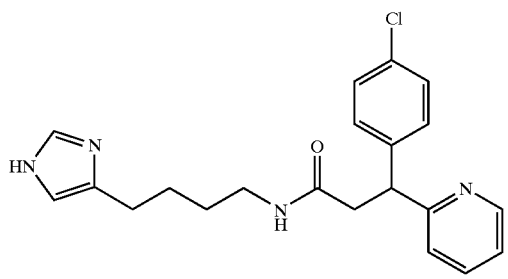

20

Compounds (6) and (10) were reacted following the same procedure as Example 12, to afford the title Compound (20); HRMS: M+1=383.1639, 383.1637.

Example 16

Preparation of Compound 21

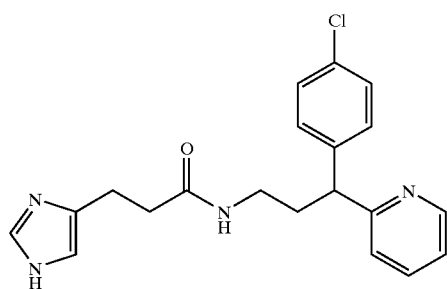

21

Compounds (4) and (14) were reacted following the same procedure as Example 12, to afford the title compound (21); HRMS: M+1=369.1482, 369.1483.

Example 17

Preparation of Compound 22

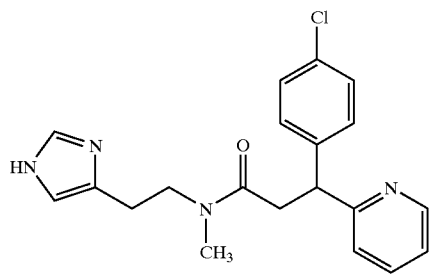

22

The trityl protected intermediate from Example 14 (200 mg) was dissolved in THF (10 mL) at room temperature and treated with NaH (27 mg, 60% dispersion in mineral oil). After stirring for 30 min. CH$_3$I (Aldrich) (95 mg) was added. After 2 hr, the reaction mixture was filtered through a plug of silica gel, eluting with ethyl acetate. The crude product was purified on a silica gel flash column (16:1:3 ethyl acetate:diethyl amine:hexane; product R$_f$=0.4) to provide the trityl-protected product (138 mg) as a white solid. This solid was detritylated following the procedure in Example 12(ii), to afford the title compound (22) (HRMS: M+1=369.1482, 369.1486).

Example 18

Preparation of Compound 23

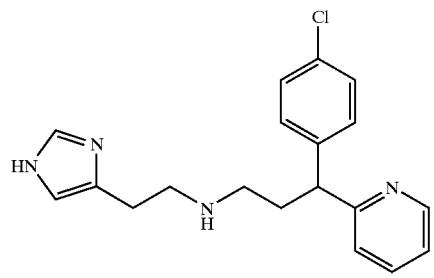

23

The trityl protected intermediate from Example 14 (145 mg) was dissolved in THF (15 mL) at room temperature and treated with LAH (2.2 mL, 1 M in THF), warmed to 40° C. and stirred overnight. The reaction was diluted with ether (20 mL) and quenched with saturated aqueous Na$_2$SO$_4$ until H$_2$ evolution had stopped, dried over solid Na$_2$SO$_4$ and filtered. Concentration and silica gel flash chromatography (90:5:5 CH$_2$Cl$_2$:CH$_3$OH:diethyl amine—100% CH$_3$OH) provided the desired amine (64 mg) which was then detritylated following the same procedure as Example 12 (ii), to afford the title compound (23) (HRMS: M+1=341.1533, 341.1531).

Example 19

Preparation of Compound 24

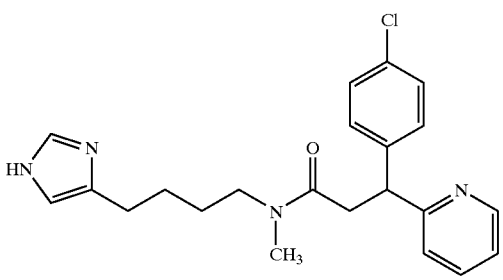

24

The trityl protected intermediate from Example 15 was reacted following the same procedure as Example 17 to afford the title compound (24) (HRMS: M+1=397.1795, 397.1791).

Example 20

Preparation of Compound 25

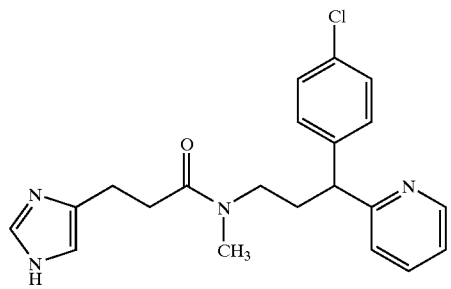

The trityl protected intermediate from Example 16 was reacted following the same procedure as Example 17 to afford the title compound (25) (HRMS: M+1=383.1639, 383.1633).

Example 21

Preparation of Compound 26

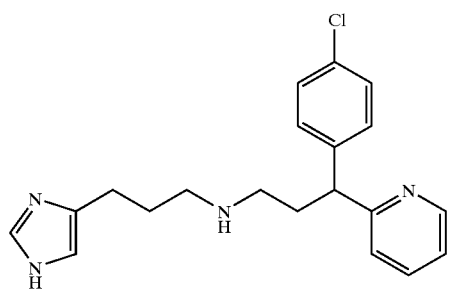

The trityl protected intermediate from Example 16 was reacted following the same procedure as Example 18 to afford the title compound (26) (HRMS: M+1=371.1639, 371.1649).

Example 22

Preparation of Compound 27

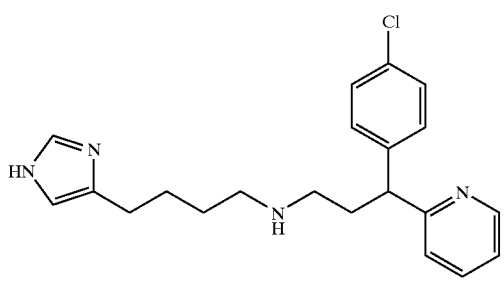

The trityl protected intermediate from Example 15 was reacted following the same procedure as Example 18 to afford the title compound (27) (HRMS: M+1=369.1846, 369.1849).

Example 23

Preparation of Compound 28

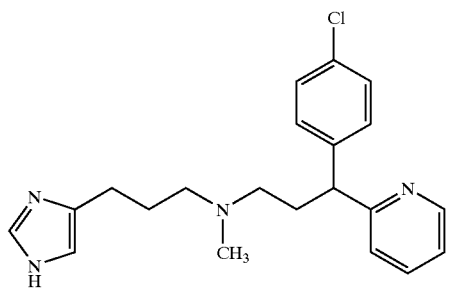

The trityl protected intermediate from Example 20 was reacted following the same procedure as Example 18 to afford the title compound (28) (HRMS: M+1=369.1846, 369.1843).

Example 24

Preparation of Compound 29

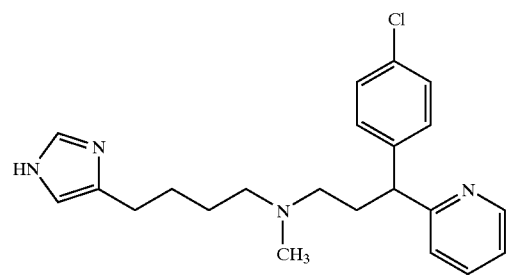

The trityl protected intermediate from Example 19 was reacted following the same procedure as Example 18 to afford the title compound (29) (HRMS: M+1=383.2002, 383.1998).

Example 25

Preparation of Compound 30

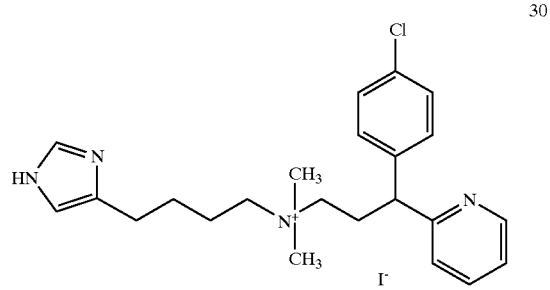

The trityl protected intermediate from Example 22 (0.8 g), was dissolved in THF (40 mL) and cooled to 0° C. CH$_3$I (0.37 g) was added and the reaction stirred for 2 hr. Triethyl amine (2 mL) was the added and the reaction stirred for 1 hr at 30° C. The reaction mixture was then diluted with CH$_2$Cl$_2$ (30 mL), washed with 10% aqueous NaHCO$_3$, then with brine and dried over solid Na$_2$SO$_4$. Concentration and purification on a silica gel flash column (10% NH$_3$ saturated CH$_3$OH in CH$_2$Cl$_2$; product R$_f$=0.3) provided the trityl-protected product (232 mg) as a white solid. This solid was detritylated following the procedure in Example 12(ii) to provide the title compound (30) (HRMS: M+1=397.2159, 397.2154).

Example 26

Preparation of Compound 31

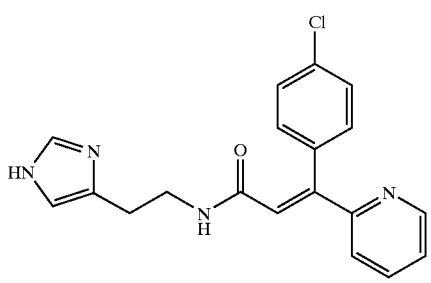

Compounds (2) and (9) were reacted following the same procedure as Example 12 to afford the title compound (31) (HRMS: M+1=353.1169, 353.1174).

Example 27

Preparation of Compound 32

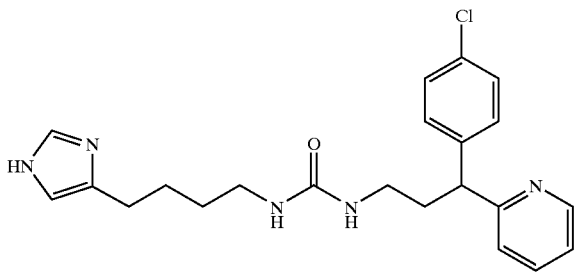

To a solution of the amine (6) (200 mg) in pyridine (2 mL) at room temperature was added the isocyanate (15) (200 mg) in one portion. The resulting mixture was stirred overnight. The reaction mixture was then concentrated under reduced pressure and purified on a silica gel flash column (5:1:4 hexane:CH$_3$OH:ethyl acetate) to provide the desired urea (170 mg) as a white solid. This solid was then detritylated following the same procedure as Example 12(ii) to provide the title compound (32) (HRMS: M+1=369.1846, 369.1849).

Example 28

Preparation of Compound 33

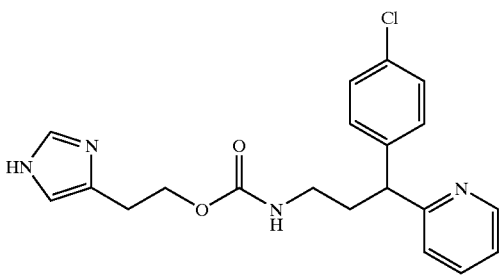

To a solution of the alcohol (7) (200 mg) in pyridine (5 mL) was added in one portion, at room temperature, the isocyanate (15) (200 mg). The resulting mixture was warmed to 75° C. and stirred for 0.5 hr. The reaction mixture was then concentrated under reduced pressure and purified on a silica gel flash column (2.5% CH$_3$OH saturated with NH$_3$ in CH$_2$Cl$_2$) to provide the trityl-protected product (351 mg) as a white solid. This solid was then detritylated following the same procedure as Example 12(ii) to provide the title compound (33) (HRMS: M+1=385.1431, 385.1429).

Example 29

Preparation of Compound 34

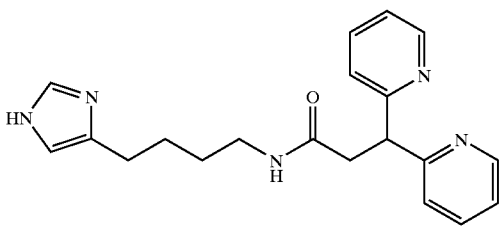

Compounds (6) and (16) were reacted following the same procedure as Example 12 to afford the title compound (34) (HRMS: M+1=350.1981, 350.1984).

Example 30

Preparation of Compound 37

(i) Preparation of Compound 36

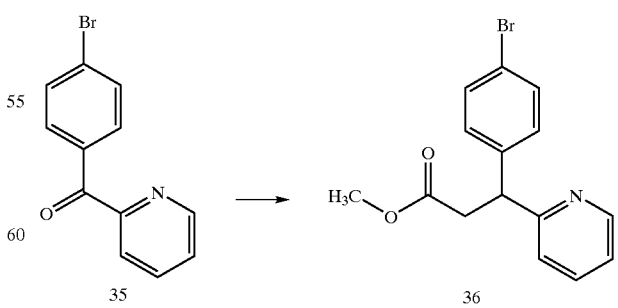

Compound (36) was prepared in the same manner as Example 7(i–iii) starting with known ketone (35) (Adamson et al. *J. Chem. Soc.* 1971, 861–864).

(ii) Preparation of Compound 37

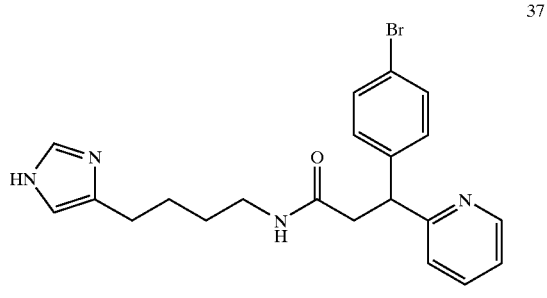

Compounds (6) and (36) were reacted following the same procedure as Example 12 to afford the title compound (37) (FABMS: M+1=427).

Example 31

Preparation of Compound 38

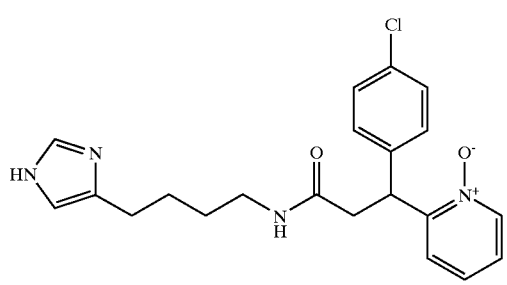

Compounds (6) and (1 1) were reacted following the same procedure as Example 12 to afford the title compound (38) (HRMS: M+1=399.1588, 399.1592).

Example 32

Preparation of Compound 39

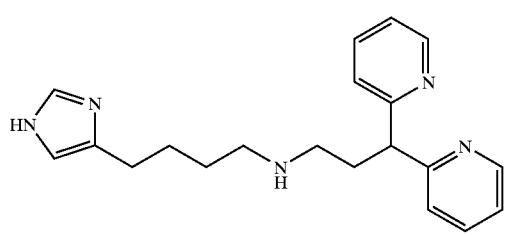

The trityl protected intermediate from Example 29 was reacted following the same procedure as Example 18 to afford the title compound (39) (HRMS: M+1=336.2188, 336.2179).

Example 33

Preparation of Compound 40

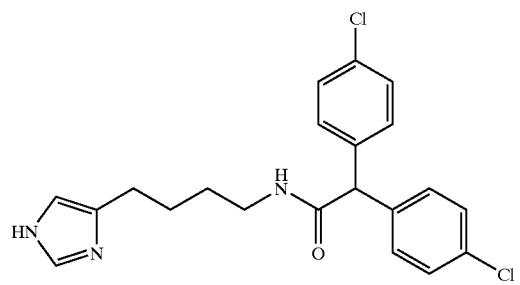

(i) A round bottom flask was charged with compound (6) (294 mg, 0.771 mmol), bis(4-chlorophenyl)acetic acid (Aldrich) (273 mg, 0.925 mmol), dimethylformamide (0.5 mL), dimethylaminopropyl-3-ethylcarbodiimide (222 mg, 1.156 mmol), HOBT (156 mg, 1.156 mmol), and triethylamine (0.42 mL, 3 mmol). The reaction was stirred at 60° C. for 18 h, then diluted with methylene chloride. The organic layer was separated and concentrated to afford crude product. Purification by chromatography on silica gel (95:5 $CH_2Cl_2$:Isopropyl alcohol eluent) afforded the desired product (Cl, M+1=658, 170 mg, 34%).

(ii) To a solution of the trityl intermediate in dioxane (6 mL) was added 4M HCl-dioxane solution (0.5 mL) at room temperature and then heated to 80° C. for 4 hr. The reaction mixture was cooled and solvent decanted. The residue was washed consecutively with ether, ethyl acetate and $CH_2Cl_2$, and dried under vacuum to afford the title compound (40) (Cl, M+1=403).

Example 34

Preparation of Compound 41

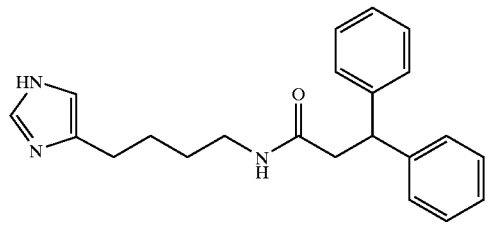

Compound (6) and 3,3-diphenylpropionic acid (Aldrich) were reacted following the same procedure as Example 35 to afford the title compound (41) (Cl, M+1=348).

Example 35

Preparation of Compound 42

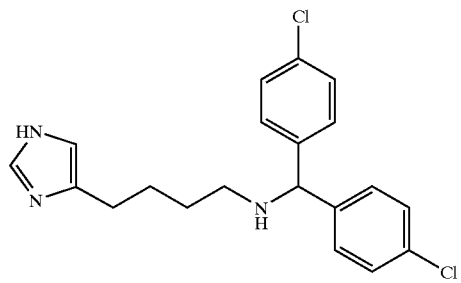

Compound (6) (300 mg, 0.787 mmol), 4,4'-dichlorobenzophenone (Aldrich) (180 mg, 0.716), and isopropanol (2.5 mL) were heated to reflux for 12 hr. The reaction was cooled to room temperature, NaBH$_4$ (44 mg, 1.6 mmole) was added and the reaction was allowed to stir at room temperature. After 2.5 hr, 1N NaOH, water and ethyl acetate were added. The crude product (269 mg, 61%) was isolated by extraction with ethyl acetate. The N-trityl intermediate was detritylated using HCl/Dioxane following the proedure in Example 35(ii) affording the

Example 36

Preparation of Compound 43

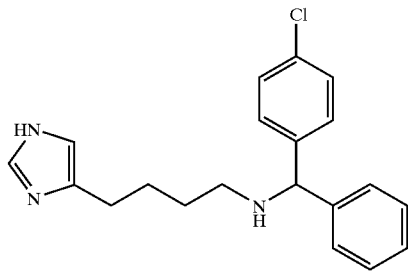

Compound (6) and 4-chlorobenzophenone (Aldrich) were reacted following the procedure in Example 38 to afford the title compound (43) (EI, 340).

Example 37

Preparation of Compound 44

(i) Preparation of Bis(4-chlorophenyl)propanoic Acid

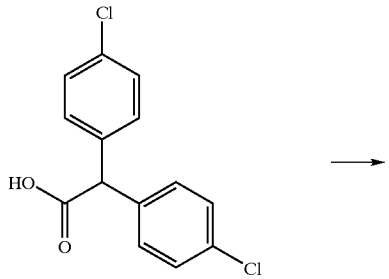

To a solution of bis(4-chlorophenyl)acetic acid (Aldrich) (9.766 g) in methanol (80 mL) was added thionyl chloride (7.6 mL) dropwise at room temperature over 0.5 hr. The reaction was stirred for 16 hr, and then concentrated in vacuo to an oil. The crude product was redissolved in ethyl acetate, washed with NaHCO$_3$ (1N), water and dried over magnesium sulfate to afford pure ester (10.20 g, 98% yield).

To a solution of the bis(4-chlorophenyl)acetic acid methyl ester (above) (3.06 g, 10.4 mmol) in THF (dry, 20 mL) was added NaH (0.38 g, 15.83 mmol) in portions. After 1 hr. hydrogen evolution ceased and methyl iodide (1 mL, 16 mmol) was added. The reaction was monitored by TLC. NaH (0.1 g, 4.1 mmol) and methyl iodide (0.5 mL, 8 mmol) were sequentially added until the starting material was consumed (as determined by TLC). The reaction was then quenched with water, partially concentrated in vacuo, and ethyl acetate added. The organic layer was separated and dried to afford methylated ester (2.18 g, 68% yield).

The above ester (0.3 g, 1.0 mmol) was hydrolyzed with lithium hydroxide hydrate (71.2 mg, 1.7 mmol) in methanol to afford 2,2 bis(4-chlorophenyl)propanoic acid.

(ii) Preparation of Compound 44

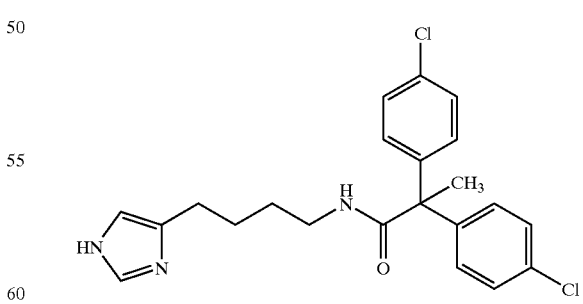

The acid from Example 40(i) above and Compound (6) were reacted following the procedure in Example 38 to afford the title compound (44) (Cl, M+1=417).

Example 38

Preparation of Compound 45

(i) Preparation of 2,2 Bis(4-chlorophenyl)acetaldehyde

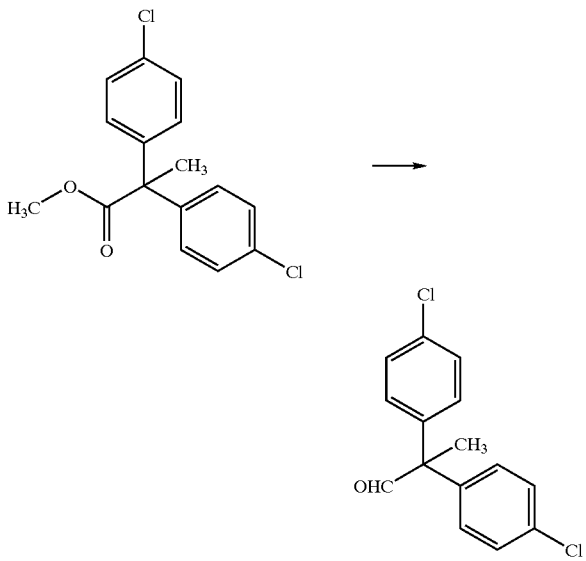

To a solution of the bis(4-chlorophenyl)acetic acid methyl ester (Example 40(i)) (2 g, 6.8 mmol) in methylene chloride (20 mL) at −78° C. was added diisobutylaluminum hydride (1M in toluene, 8.1 mL, 8.1 mmol) dropwise. The reaction was allowed to warm to −60° C. over 1 hr. and then warm to room temperature for an additional 1 hr. The reaction was quenched by the addition of methanol, and then transferred to a separatory funnel. Water and additional methylene chloride were added and the organic layer separated and dried to afford crude aldehyde. Further purification on silica gel (1:1 hexane:ethyl acetate eluent) afforded pure aldehyde (0.9 g, 50% yield).

(ii) Preparation of Compound 45

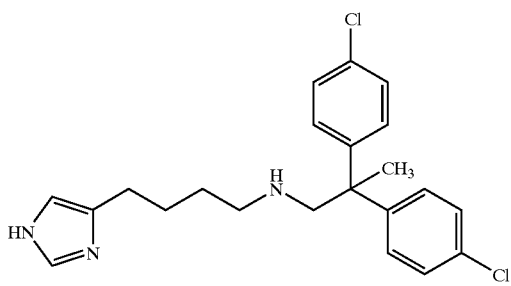

A flask was charged with compound (6) (0.6 g, 1.56 mmol), 2,2 bis(4-chlorophenyl)acetaldehyde (Example 41(i)) (0.4 g, 1.43 mmol), and isopropanol (5 mL) and heated to reflux for 3 hr. The reaction was cooled to room temperature, and $NaBH_4$ (87 mg, 2.3 mmole) was added. After 12 h., 1N NaOH, water and ethyl acetate were added. The crude product (185 mg, 20%) was isolated by extraction with ethyl acetate. The N-trityl intermediate was then detritylated following the procedure found in Example 35 (ii) affording the desired product compound (45) (Cl, M+1= 403).

General Procedure for H1-Receptor Binding Assay

The procedure used was based on that disclosed in V. T. Tran, R. S. L. Chang, and S. hr. Snyder, "Histamine $H_1$ receptors identified in mammalian brain membranes with [H-3]mepyramine", *Proc. Natl. Acad. Sci. U.S.A* 75 (1978) 6290–6294.

I. Tissue Preparation Protocol for Histamine $H_1$ Receptor Binding Assay

1. The tissue source was male Sprague-Dawley rat brain. These were purchased stripped and frozen (available from Rockland Corporation, Gilbertsville, Pa.). The buffer used was ice-cold 50 mM Tris-HCl, pH 7.5. (The pH was determined at 25° C.)
2. The brains were spread out on plastic wrap on the benchtop and allowed to thaw for 10–15 min. After this, everything was kept ice-cold.
3. Two brains were put in each 50 mL round bottom centrifuge tube and 25 mL of buffer was added. Then they were broken up with a Polytron (from Brinkmann Instruments, Westbury, N.Y.) equipped with a PT-10 tip at setting 6 for 30 sec.
4. The volume in the tube was brought up to 45 mL and mixed and the particulate material was centrifuged at 1000×g (3000 rpm, SS-34 rotor) for 10 min to remove nuclei and unbroken cells.
5. Pellets were discarded and the supernatants were centrifuged 10 min at 50,000×g (20,000 rpm, SS-34 rotor).
6. The high-speed pellets were resuspended in a volume of Tris buffer equal to the original (4 mL), the contents of all tubes were pooled, and a sample was taken for BCA protein assay. The material was aliquotted, 45 mL per round-bottom tube, and the resuspension was recentrifuged. The yield of protein was approximately 20 mg/brain, so there was about 40 mg of protein per tube.
7. Pellets were frozen at −80° C.

II. $H_1$ Histamine Receptor Binding Assay

Materials: 96-well, deep-well, polypropylene plates, [$^3$H] pyrilamine, 20–30 Ci/mmol, from Dupont NEN Life Science Products, Boston, Mass.), chlorpheniramine maleate (from Schering-Plough Corporation, Kenilworth, N.J.) as standard, stored as frozen $10^{-5}$, $10^{-6}$, $10^{-7}$, $10^{-8}$M solutions.

1. FDCL and comparative compounds for assay were independently solubilized at 1 mg/ml DMSO by vortexing, or if necessary by sonication. The first dilution, 100-fold, was made in 50 mM Tris-HCl, pH 7.5, at room temperature. The three or four subsequent ten-fold serial dilutions were made in 1% DMSO/50 mM Tris-HCl, pH 7.5. Drug solutions and assay plates were kept at room temperature during the course of the assay set up.
2. Test compounds were assayed at four or five concentrations: 1, 0.1, 0.01, 0.001, and 0.0001 μg/ml. Twenty μl of drug solution was pipeted into each of three wells. A chlorpheniramine maleate standard was assayed at $10^{-9}$ to $10^{-6}$ M, 20 μl of each of the appropriate solutions being pipeted into triplicate wells. Total and nonspecific ($10^{-6}$ M chlorpheniramine maleate) binding were determined at least in quadruplicate. For total binding, 20 μl of buffer was pipeted and for nonspecific 20 μl of $10^{-5}$ M chlorpheniramine maleate was pipeted into each well.
3. [$^3$H]Pyrilamine was diluted approximately 2000-fold with ice-cold mM Tris-HCl, pH 7.5 (to a working concentration of 20–25 nM), and put on ice.
4. A frozen tissue pellet was thawed in a 25° C. water bath, resuspended in 50 mM Tris-HCl, pH 7.5, at 1.7–2 mg/ml by brief break-up on the Polytron, and put on ice.

5. Twenty μl of diluted [³H]pyrilamine was added to each well.
6. One hundred fifty μl of tissue suspension was added to each well.
7. The top of the plate was covered and it was placed in a 25° C. shaking water bath (about 60 oscillations/min) for 30 min.
8. Samples were filtered on a Tomtec Mach 2 harvester (available from Tomtec Corporation, Orange, Conn.) through a GF/B filter mat (from Wallac, Inc., Gaithersburg, Md.) presoaked in 0.3% polyethylenimine. Each sample was thrice washed with ice-cold 50 mM Tris-HCl, pH 7.5 dried 20 sec on the Tomtec, and dried 3–4 min in a microwave oven on a paper towel. The filter was impregnated with MELTILEX brand wax scintillant (from Wallac Corporation) and counted on a Betaplate scintillation counter (from Wallac Corporation).
9. Specific binding was determined as the difference between total and nonspecific binding. The percent inhibition in the presence of inhibitor or standard was determined using the formula:

[1-(sample binding-nonspecific binding)/specific binding]×100

For compounds that inhibit more than 50% at 1 μg/ml, an $IC_{50}$ value was interpolated from proximate concentrations. The value was converted to a nM value using the compound formula weight and a $K_i$ value was calculated using the equation of Cheng and Prusoff ($K_i=IC_{50}/(1+[L]/K_D)$), [Y-C. Cheng and W. H. Prusoff, "Relationship between the inhibitory constant ($K_i$) and the concentration of inhibitor which causes 50 percent inhibition ($IC_{50}$) of an enzymatic reaction", *Biochem. Pharmacol.* 22 (1973) 3099–3108]. Lower value of $K_i$ indicates greater binding affinity.

General Procedure for H₃-Receptor Binding Assay

The source of the H₃ receptors in this experiment was guinea pig brain. The animals weighed 400–600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 μg/ml with 0.1% DMSO. Membranes were then added (400 μg of protein) to the reaction tubes. The reaction was started by the addition of 3 nM [³H]R-α-methyl histamine (8.8 Ci/mmol) or 3 nM [³H]N^α-methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM). The results are given in the Table 1 for the HCl salt of the indicated compound.

TABLE 1

| STRUCTURE | H3 Ave Ki (nM) | H1 Ave Ki (nM) |
|---|---|---|
| 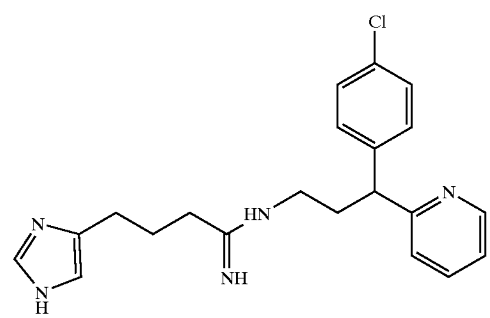 | 29 | 201 |
| 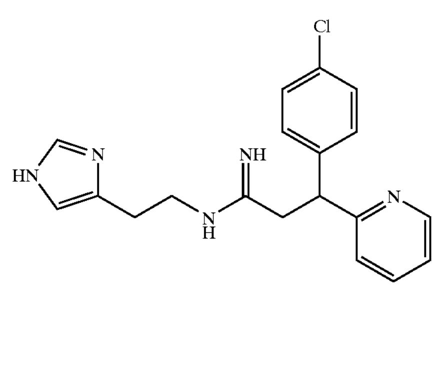 | 8 | NT |

TABLE 1-continued

| STRUCTURE | H3 Ave Ki (nM) | H1 Ave Ki (nM) |
|---|---|---|
| (structure) | 16 | NT |
| (structure) | 0.8 | NT |
| (structure) | 1 | NT |
| (structure) | 56 | 600 |
| (structure) | 6.5 | NT |

TABLE 1-continued

| STRUCTURE | H3 Ave Ki (nM) | H1 Ave Ki (nM) |
|---|---|---|
| (imidazole-CH2CH2-C(=O)-NH-CH2CH2-CH(4-chlorophenyl)(2-pyridyl)) | 510 | NT |
| (imidazole-CH2CH2-C(=O)-N(CH3)-CH2CH2-CH(4-chlorophenyl)(2-pyridyl)) | 260 | 1000 |
| (imidazole-CH2CH2CH2-NH-CH2CH2-CH(4-chlorophenyl)(2-pyridyl)) | 240 | NT |
| (imidazole-(CH2)4-NH-CH2CH2-CH(4-chlorophenyl)(2-pyridyl)) | 10 | 254 |
| (imidazole-CH2CH2CH2-N(CH3)-CH2CH2-CH(4-chlorophenyl)(2-pyridyl)) | 120 | 10 |

TABLE 1-continued
| STRUCTURE | H3 Ave Ki (nM) | H1 Ave Ki (nM) |
|---|---|---|
| 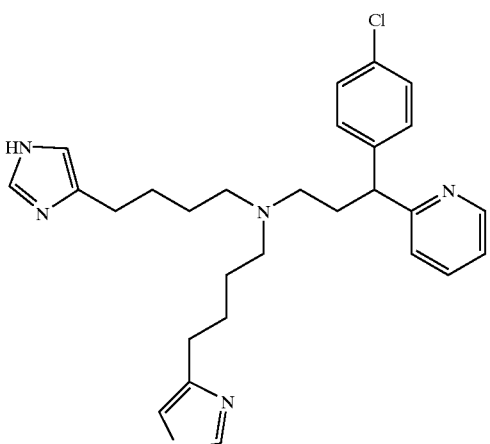 | 23 | 83.5 |
| 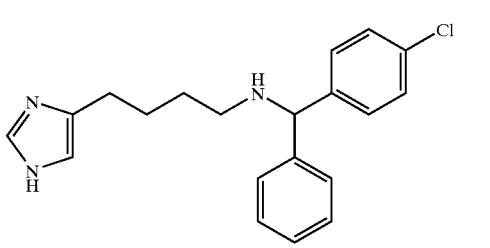 | 6 | NT |
| 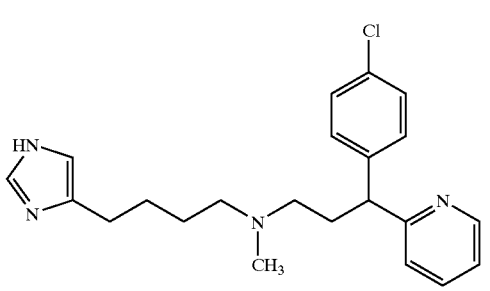 | 15 | 7 |
| 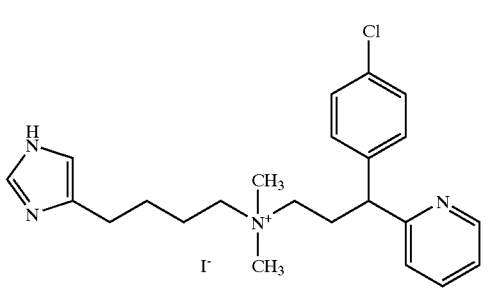 | 160 | 120 |
| 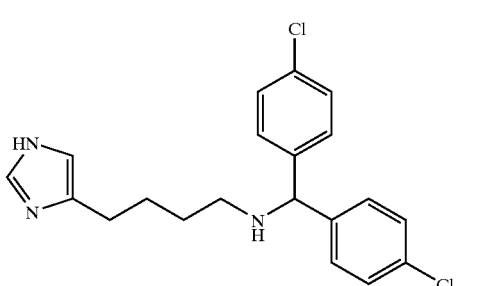 | 2 | NT |

TABLE 1-continued

| STRUCTURE | H3 Ave Ki (nM) | H1 Ave Ki (nM) |
|---|---|---|
| 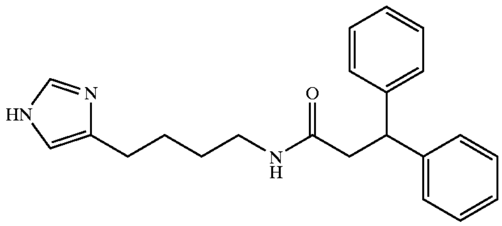 | 36 | NT |
| 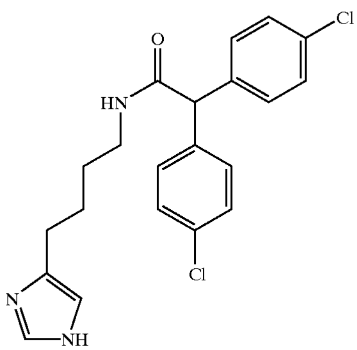 | 33.5 | NT |
| 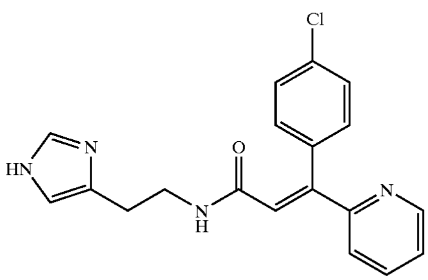 | 37 | NT |
| 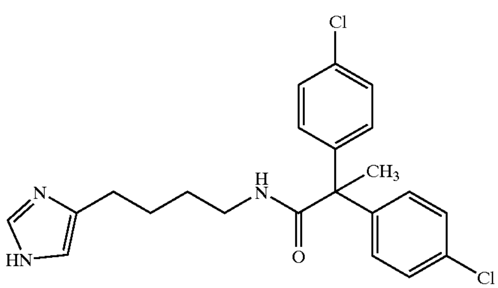 | 22.5 | NT |
| 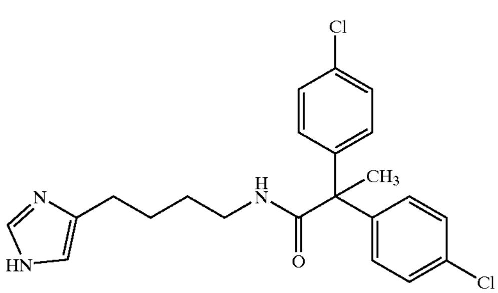 | 110 | NT |

TABLE 1-continued

| STRUCTURE | H3 Ave Ki (nM) | H1 Ave Ki (nM) |
|---|---|---|
| 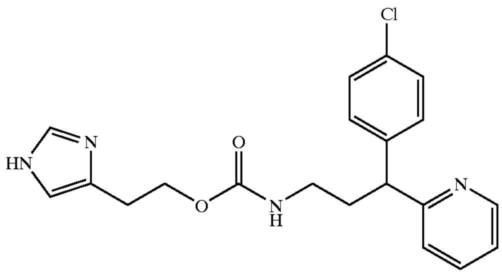 | 260 | NT |
| 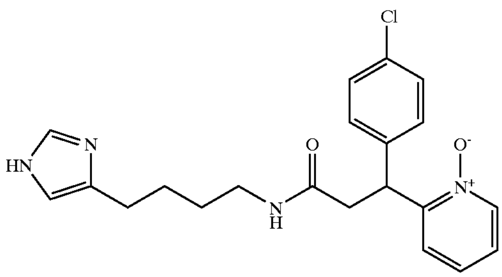 | 8.5 | NT |
| 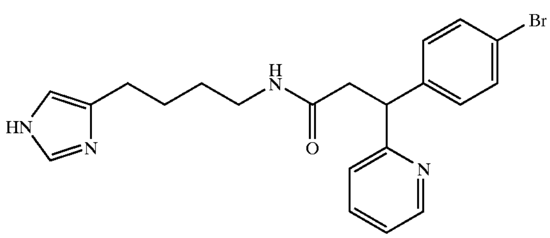 | 50 | NT |

NT = Not Tested

From these test results and the background knowledge about the compounds described in the references in the section "Background of the Invention", it would be apparent to the skilled artisan that the compounds of the invention have utility in treating inflammation, allergy, diseases of the GI-tract, cardiovascular disease, disturbances of the central nervous system and the like

What is claimed is:

1. A compound, or an enantiomer, a stereoisomer or tautomer thereof, or a pharmaceutically acceptable salt or solvate of said compound, with said compound having the general structure shown in Formula I:

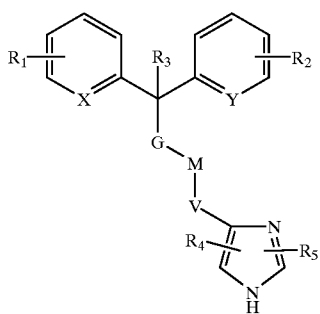

Formula I wherein
G is selected from the group consisting of $C_1$–$C_6$ alkyl or a bond;
M is a moiety selected from the group consisting of —C=C—, —C≡C—, —C(=NR$^7$)—NR$^6$—, —NR$^6$—C(=NR$^7$)—, —NR$^6$—C(O)—NR$^6$—, —NR$^6$—C(O)—O—, —O—C(O)—NR$^6$—, —NR$^6$—C(O)—, —C(O)—NR$^6$—, —O—, —NR$^6$—, —C(O)—, —N$^+$R$^6$R$^8$—, and

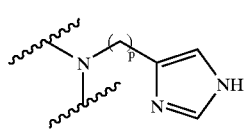

p is 1–6
V is $C_1$–$C_6$ alkyl;
X and Y may be the same or different and are independently selected from the group consisting of N, CH, or N-oxide, with the proviso that at least one of X and Y is N or N-oxide;
$R^1$ and $R^2$ may each number 1–4 and are independently selected from the group consisting of hydrogen, lower alkyl, lower alkoxy, halogen, polyhalolower alkyl, —OH, —N(R$^6$)$_2$, —NO$_2$, —CN, —COOR$^6$, —CONR$^6$R$^8$, and —NR$^6$—C(O)—R$^7$(wherein R$^7$ is not —OH or —CN);

R³ is selected from hydrogen, lower alkyl, lower alkoxy, hydroxyl, polyhalolower alkyl, and a bond forming a double bond towards the moiety G when G is $C_1$–$C_6$ alkyl;

R⁴ and R⁵ are independently selected from the group consisting of hydrogen, lower alkyl, and polyhalolower alkyl;

R⁶ and R⁸ are independently selected from hydrogen, lower alkyl, aralkyl, alkylaryl, polyhalolower alkyl, substituted or unsubstituted phenyl; and substituted or unsubstituted benzyl; and R⁷ is selected from H, OH, alkoxy, cyano, phenyl, substituted phenyl, benzyl, and substituted benzyl;

with the proviso that when G is a bond, M is not —NR⁶C(O)O—, and with the proviso that when G is a bond and when M is either —O— or —O—C(O)—NR⁶—, then one of X and Y is N; and with the further proviso that when R³ is —OH or alkoxyl, and G is a bond, then M≠O or NR⁶.

2. The compound of claim 1, wherein $R_4$=$R_5$=H.

3. The compound of claim 2, wherein $R_6$ and $R_7$ are H or lower alkyl.

4. The compound of claim 2, wherein $R_1$ and $R_2$ are independently selected from H, halogen, hydroxy or lower alkoxy.

5. The compound of claim 2, wherein M is selected from the group consisting of —C(=NH)—NH—; —NH—C(=NH)—; —C(O)—NH—; —C(O)—N(CH₃)—; —NH—; —N(CH₃)—; —NHCO—; —N(CH₃)—CO—; —NHC(=O)—NH—; —NHC(=O)—O—; —NH—C(=N—CN)—NH—; and —O—C(=O)—NH—.

6. The compound of claim 5, wherein R¹ and R² are H, halogen, hydroxy or alkoxy; and R³ is H, lower alkyl or a bond forming a double bond towards moiety G.

7. The compound of claim 6 wherein R³=H, M is —NH—, —N(alkyl)—, —C(O)NH—, —C(=NH)NH—, —C(O)N(alkyl)—.

8. A composition comprising a compound of claim 1.

9. A pharmaceutical composition for use in treating inflammation, allergy, allergic rhinitis, congestion, or allergy-induced airway responses, said composition comprising as an active ingredient a compound of claim 1.

10. The composition of claim 8 additionally comprising a pharmaceutically acceptable carrier.

11. A method of treating inflammation, allergy, nasal congestion, or allergy-induced airway responses, said method comprising administering to a mammalian patient in need of such treatment a pharmaceutical composition which comprises therapeutically effective amounts of a compound of claim 1.

12. A method of preparing a pharmaceutical composition for treating inflammation, allergy, nasal congestion, or allergy-induced airway responses, said method comprising bringing into intimate contact a compound of claim 1 and a pharmaceutically acceptable carrier.

13. A compound exhibiting $H_3$ antagonist activity, or an enantiomer, a stereoisomer or tautomer of said compound, or a pharmaceutically acceptable salt or solvate of said compound, said compound being selected from the compounds of structures listed below:

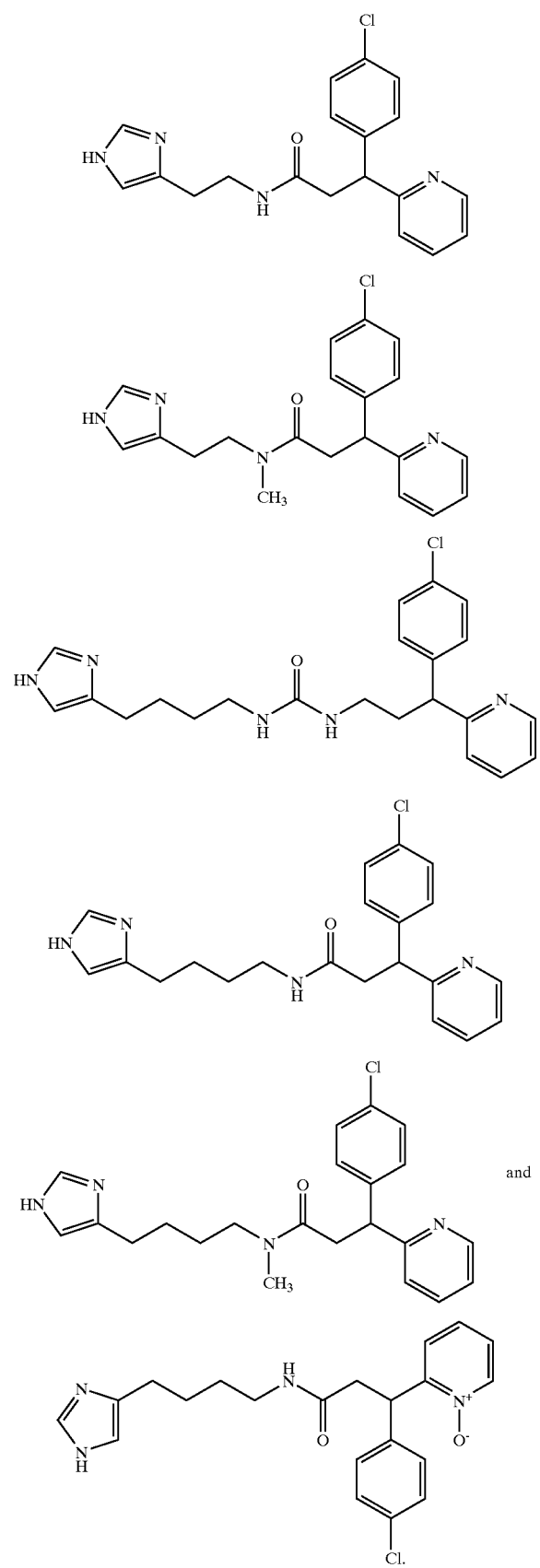

14. A compound exhibiting both $H_1$ and $H_3$ antagonist activity, or an enantiomer, a stereoisomer or a tautomer of said compound, or pharmaceutically acceptable salt or a solvate of said compound, said compound being selected from the compounds of structures listed below:

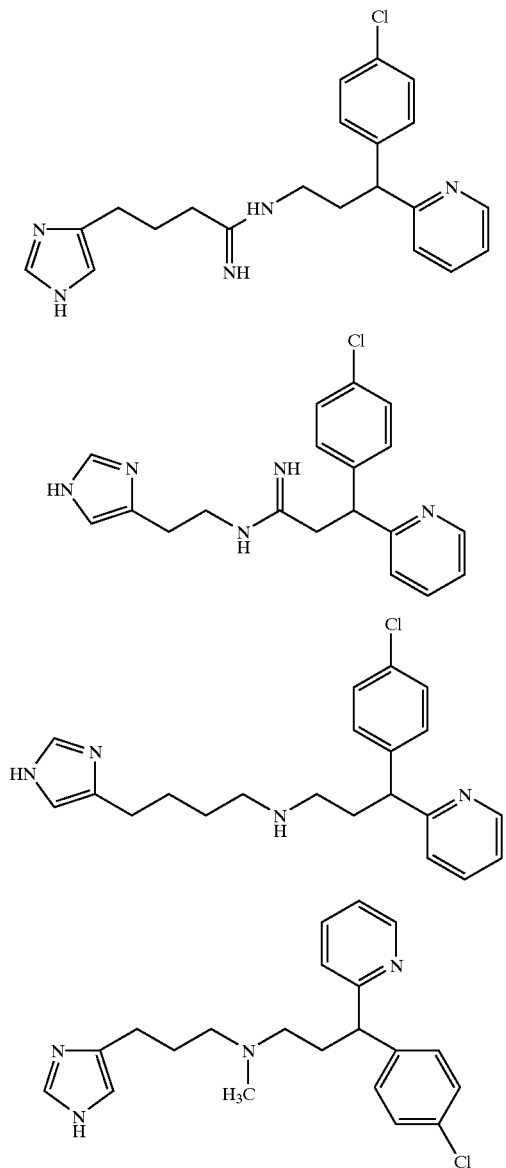

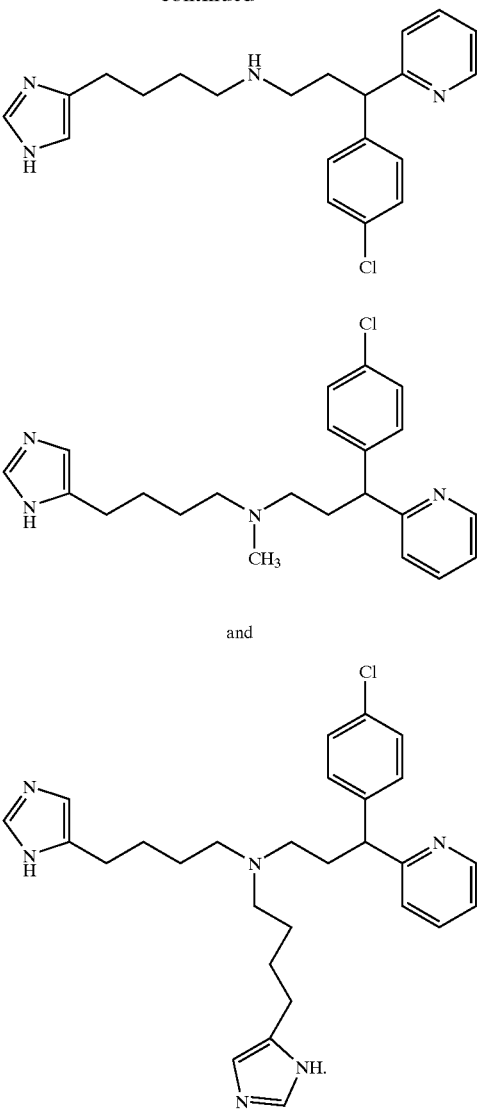

15. A pharmaceutical composition for treating inflammation, allergy, nasal congestion, or allergy-induced airway responses, said composition comprising therapeutically effective amount of a compound of claim 14 and a pharmaceutically acceptable carrier.

* * * * *